US007169771B2

(12) United States Patent
Hynes et al.

(10) Patent No.: US 7,169,771 B2
(45) Date of Patent: Jan. 30, 2007

(54) THIAZOLYL-BASED COMPOUNDS USEFUL AS KINASE INHIBITORS

(75) Inventors: John Hynes, Washington Crossing, PA (US); Hong Wu, New Hope, PA (US); Katerina Leftheris, Skillman, NJ (US); Chunjian Liu, Pennington, NJ (US); Jagabandhu Das, Mercerville, NJ (US); Robert V. Moquin, East Brunswick, NJ (US)

(73) Assignee: Bristol-Myers Squibb Company, Princton, NJ (US)

( * ) Notice: Subject to any disclaimer, the term of this patent is extended or adjusted under 35 U.S.C. 154(b) by 476 days.

(21) Appl. No.: 10/773,790

(22) Filed: Feb. 6, 2004

(65) Prior Publication Data

US 2004/0220233 A1    Nov. 4, 2004

Related U.S. Application Data

(60) Provisional application No. 60/445,410, filed on Feb. 6, 2003.

(51) Int. Cl.
*A61K 31/425*    (2006.01)
*C07D 277/20*    (2006.01)

(52) U.S. Cl. .................................. 514/194; 548/370
(58) Field of Classification Search ............... 514/370; 548/194
See application file for complete search history.

(56) References Cited

U.S. PATENT DOCUMENTS

| | | | |
|---|---|---|---|
| 4,200,750 | A | 4/1980 | Warner, Jr. et al. |
| 5,712,279 | A | 1/1998 | Biller et al. |
| 5,739,135 | A | 4/1998 | Biller et al. |
| 5,760,246 | A | 6/1998 | Biller et al. |
| 6,184,231 | B1 | 2/2001 | Hewawasam et al. |
| 6,262,094 | B1 | 7/2001 | Hoefle et al. |
| 6,262,096 | B1 | 7/2001 | Kim et al. |
| 6,548,529 | B1 | 4/2003 | Robl et al. |
| 6,596,746 | B1 | 7/2003 | Das et al. |
| 6,605,599 | B1 | 8/2003 | Vite et al. |
| 6,706,720 | B2 | 3/2004 | Atwal et al. |
| 6,720,346 | B2 * | 4/2004 | Chu et al. ............. 514/370 |
| 2002/0065270 | A1 | 5/2002 | Moriarty et al. |
| 2002/0137747 | A1 | 9/2002 | Moriarty et al. |
| 2003/0114504 | A1 | 6/2003 | Webster et al. |
| 2004/0024208 | A1 | 2/2004 | Das et al. |
| 2004/0039033 | A1 | 2/2004 | Atwal et al. |
| 2004/0054186 | A1 | 3/2004 | Das et al. |
| 2004/0073026 | A1 | 4/2004 | Das et al. |
| 2004/0077875 | A1 | 4/2004 | Das et al. |

FOREIGN PATENT DOCUMENTS

| | | |
|---|---|---|
| WO | WO 00/62778 | 10/2000 |
| WO | WO 01/10865 | 2/2001 |
| WO | WO 02/96905 | 3/2001 |
| WO | WO 01/35959 | 5/2001 |
| WO | WO 01/70671 | 9/2001 |
| WO | WO 01/74811 | 10/2001 |
| WO | WO 02/45652 | 6/2002 |

OTHER PUBLICATIONS

Ahn, H.-S. et al., "Potent Tetracyclic Guanine Inhibitors of PDE1 and PDE5 Cyclic Guanosine Monophosphate Phosphodiesterases with Oral Antihypertensive Activity", J. Med. Chem., vol. 40, No. 14, pp. 2196-2210 (1997).

Henry, J.R. et al., "p38 mitogen-activated protein kinase as a target for drug discovery", Drugs of the Future, vol. 24, No. 12, pp. 1345-1354 (1999).

Moreland, L.W. et al., "Etanercept Therapy in Rheumatoid Arthritis: A Randomized, Controlled Trial", Ann. Intern. Med., vol. 130, No. 6, pp. 478-486 (1999).

Rankin, E.C.C. et al., "The Therapeutic Effects of an Engineered Human Anti-Tumour Necrosis Factor Alpha Antibody (CDP571) in Rheumatoid Arthritis", British Journal of Rheumatology, vol. 34, No. 4, pp. 334-342 (1995).

Raingeaud, J. et al., "MKK3- and MKK6-Regulated Gene Expression Is Mediated by the p38 Mitogen-Activated Protein Kinase Signal Transduction Pathway", Molecular and Cellular Biology, vol. 16, No. 3, pp. 1247-1255 (1996).

Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).

Zhao, R. et al., "A new facile synthesis of 2-aminothiazole-5-carboxylates", Tetrahedron Letters, vol. 42, pp. 2101-2102 (2001).

* cited by examiner

*Primary Examiner*—Kamal A. Saeed
(74) *Attorney, Agent, or Firm*—Joseph C. Wang; Anastasia P. Winslow

(57) ABSTRACT

The present invention provides thiazolyl-based compounds of formula (I), (I)

useful for treating p38 kinase-associated conditions, wherein ring A is phenyl or pyridyl, and X, Y, B, $R^2$, $R^3$, $Z^1$ m and n are as defined herein. The invention further pertains to pharmaceutical compositions containing at least one compound according to the invention useful for treating p38 kinase-associated conditions, and methods of inhibiting the activity of p38 kinase in a mammal.

2 Claims, No Drawings

THIAZOLYL-BASED COMPOUNDS USEFUL AS KINASE INHIBITORS

RELATED INVENTIONS

This application claims the benefit of U.S. provisional application Ser. No. 60/445,410, filed Feb. 6, 2003.

FIELD OF THE INVENTION

This invention relates to thiazolyl-based compounds useful for treating p38 kinase-associated conditions. The invention further pertains to pharmaceutical compositions containing at least one compound according to the invention for treating p38 kinase-associated conditions, and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, Vol. 24 (1999), at pp. 1345–54; Salituro et al, *Curr. Med. Chem.*, Vol. 6 (1999), at pp. 807–823]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, Vol. 34 (1995), at pp. 334–42], and soluble TNF-α receptor-Fc fusion protein (Etanercept) [Moreland et al., *Ann. Intern. Med.*, Vol. 130 (1999), at pp. 478–86].

The biosynthesis of TNF-α occurs in many cell types in response to an external stimulus, such as, for example, a mitogen, an infectious organism, or trauma. Important mediators of TNF-α production include the mitogen-activated protein (MAP) kinases, a family of Ser/Thr protein kinases that activate their substrates by phosphorylation. The MAP kinases are activated in response to various stress stimuli, including but not limited to proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that these inhibitors are effective in treating those diseases.

The present invention provides benzamide-thiazolyl compounds, useful as kinase inhibitors, in particular, as inhibitors of p38 kinase. Thiazolyl derivatives that reportedly inhibit p38 kinase and TNF-α for use in treating inflammatory diseases are disclosed in WO 01/74811 and WO 01/10865 to Takeda Chem. Indus., WO 01/35959 to Astrazeneca AB, and WO 02/096905 to Vertex Pharmaceuticals. Tyrosine kinase inhibitors having a thiazolyl component are disclosed in WO 02/45652 to Merck & Co., Inc., and WO 00/62778 to Bristol-Myers Squibb Company. Aminothiazolyl compounds useful as cyclin dependent kinase inhibitors are described in U.S. Pat. No. 6,262,096 to Bristol-Myers Squibb Company.

SUMMARY OF THE INVENTION

The invention is directed to compounds having the formula (I), useful as inhibitors of p38 kinase,

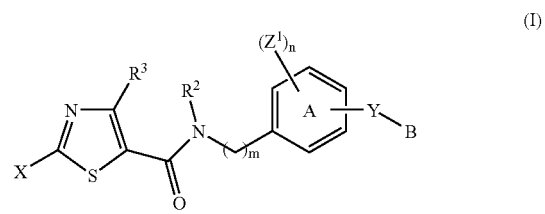

and enantiomers, diastereomers, pharmaceutically-acceptable salts, and solvates thereof, wherein, ring A is phenyl or pyridyl;

Y is $-C(=O)NR^1-$ or $-NR^1C(=O)-$ and is attached to the phenyl or pyridyl ring in the meta or para position;

$R^1$ is
  (a) hydrogen, or
  (b) alkyl, cycloalkyl, aryl(alkyl), (heteroaryl)alkyl, (heterocyclo)alkyl or (cycloalkyl)alkyl, any of which may be optionally substituted as valence allows with $Z^{1a}$, $Z^{2a}$ and up to two $Z^{3a}$;

B is
  (a) hydrogen or hydroxy, or
  (b) alkyl, cycloalkyl, (cycloalkyl)alkyl, alkenyl, alkoxy, (alkoxy)alkyl, aryl, (aryl)alkyl, heteroaryl, (heteroaryl)alkyl, heterocyclo or (heterocyclo)alkyl, any of which may be optionally substituted as valence allows with $Z^{1b}$, $Z^{2b}$ and up to two $Z^{3b}$;

$R^2$ is
  (a) hydrogen, or
  (b) alkyl, cycloalkyl, aryl(alkyl), (heteroaryl)alkyl, (heterocyclo)alkyl, or (cycloalkyl)alkyl, any of which may be optionally substituted as valence allows with $Z^{1c}$, $Z^{2c}$ and up to two $Z^{3c}$;

$R^3$ is hydrogen, alkyl, haloalkyl, alkoxy, (alkoxy)alkyl, hydroxy, (hydroxy)alkyl, halogen, cyano, or $-NR^6R^7$;

X is

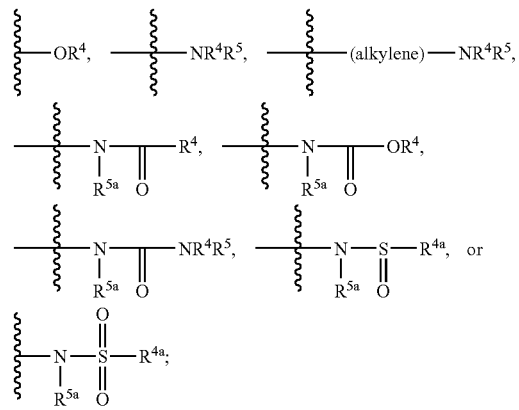

$R^4$, $R^5$ and $R^{5a}$ are independently
  (a) hydrogen, or
  (b) alkyl, cycloalkyl, (cycloalkyl)alkyl, (alkoxy)alkyl, alkenyl, aryl, (aryl)alkyl, heteroaryl, (heteroaryl)alkyl, heterocyclo or (heterocyclo)alkyl, any of which may be optionally substituted as valence allows with $Z^{1d}$, $Z^{2d}$ and up to two $Z^{3d}$; or
  (c) $R^4$ and $R^5$ together with the nitrogen atom to which they are bonded may optionally combine to form a heterocyclo ring which may be optionally substituted as valence allows with $Z^{1d}$, $Z^{2d}$ and up to two $Z^{3d}$;

$R^{4a}$ is alkyl, cycloalkyl, (cycloalkyl)alkyl, alkoxy, (alkoxy)alkyl, alkenyl, aryl, (aryl)alkyl, heteroaryl, (heteroaryl)alkyl, heterocyclo, or (heterocyclo)alkyl, any of which may be optionally substituted as valence allows with $Z^{1d}$, $Z^{2d}$ and up to two $Z^{3d}$;

$R^6$ and $R^7$ are independently
  (a) hydrogen or
  (b) alkyl, cycloalkyl, (cycloalkyl)alkyl, aryl, (aryl)alkyl, heteroaryl, (heteroaryl)alkyl, heterocyclo or (heterocyclo)alkyl, any of which may be optionally substituted as valence allows with $Z^{1e}$, $Z^{2e}$ and up to two $Z^{3e}$;

$Z^{1-1e}$, $Z^{2a-2e}$, and $Z^{3a-3e}$ are optional substituents independently selected from
  (1) $R^{10}$, where $R^{10}$ is
    (i) alkyl, (hydroxy)alkyl, (alkoxy)alkyl, alkenyl, alkynyl, cycloalkyl, (cycloalkyl)alkyl, aryl, (aryl)alkyl, heterocyclo, (heterocylco)alkyl, heteroaryl, or (heteroaryl)alkyl;
    (ii) a group (i) which is itself substituted by one to four of the same or different groups (i); or
    (iii) a group (i) or (ii) which is independently substituted by one to four of the following groups (2) to (12);
  (2) —$OR^{11}$,
  (3) —$SR^{11}$,
  (4) —$C(O)_r R^{11}$ or —O—$C(O)R^{11}$;
  (5) —$SO_3H$, —$S(O)_r R^{16}$, or $S(O)_r N(R^{11})R^{12}$,
  (6) halo,
  (7) cyano,
  (8) nitro,
  (9) —$U^1$—$NR^{12}R^{13}$,
  (10) —$U^1$—$N(R^{11})$—$U^2$—$NR^{12}R^{13}$,
  (11) —$U^1$—$N(R^{14})$—$U^2$—$R^{11}$,
  (12) oxo;

$U^1$ and $U^2$ are each independently
  (1) a single bond,
  (2) —$U^3$—$S(O)_t$—$U^4$—,
  (3) —$U^3$—$C(O)$—$U^4$—,
  (4) —$U^3$—$C(S)$—$U^4$—,
  (5) —$U^3$—O—$U^4$—,
  (6) —$U^3$—S—$U^4$—,
  (7) —$U^3$—O—$C(O)$—$U^4$—,
  (8) —$U^3$—$C(O)$—O—$U^4$—, or
  (9) —$U^3$—$C(=NR^{15})$—$U^4$;

$U^3$ and $U^4$ are each independently
  (1) a single bond,
  (2) alkylene,
  (3) alkenylene, or
  (4) alkynylene;

$R^{11}$, $R^{12}$, $R^{13}$, $R^{14}$, $R^{15}$ and $R^{16}$
  (1) are each independently hydrogen, alkyl, (hydroxy)alkyl, (alkoxy)alkyl, alkenyl, alkynyl, cycloalkyl, (cycloalkyl)alkyl, aryl, (aryl)alkyl, heterocyclo, (heterocylco)alkyl, heteroaryl, or (heteroaryl)alkyl, any of which is unsubstituted or substituted with one to four groups listed below for $R^{20}$; except $R^{16}$ is not hydrogen; or
  (2) $R^{12}$ and $R^{13}$ may be taken together to form a 3- to 8-membered saturated or unsaturated ring together with the atoms to which they are attached, which ring is unsubstituted or substituted with one to four groups listed below for $R^{20}$, or
  (3) $R^{12}$ and $R^{13}$ together with the nitrogen atom to which they are attached may combine to form a group —N=C $R^{17}R^{18}$ where $R^{17}$ and $R^{18}$ are each independently hydrogen, alkyl, or alkyl substituted with a group $R^{20}$;

$R^{20}$ is alkyl, halogen, cyano, hydroxy, —O(alkyl), SH, —S(alkyl), amino, alkylamino, haloalkyl, or a lower alkyl substituted with cyano, hydroxy, or alkoxy;

m is 0 or 1;
n is 0, 1, 2, or 3; and
t is 1 or 2.

Also included in the invention are pharmaceutical compositions containing compounds according to formula (I), for treating inflammatory and immune conditions, and methods of inhibiting p38 kinase in a mammal comprising administering to the mammal at least one compound according to formula (I), alone or together with another pharmaceutically-active agent.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are most preferred.

The term "substituted alkyl" refers to an alkyl group substituted with one or more substituents (preferably 1 to 4 substituents, even more preferably 1 to 2 substituents) at any available point of attachment. Exemplary substituents may be selected from one or more (preferably 1 to 3) of the following groups:
  (i) halogen (e.g., a single halo substituent or multiple halo substitutents forming, in the latter case, groups such as a perfluoroalkyl group or an alkyl group bearing $Cl_3$ or $CF_3$), haloalkoxy, cyano, nitro, oxo (=O), —$OR_a$, —$SR_a$, —$S(=O)R_e$, —$S(=O)_2R_e$, —$S(=O)_3H$, —$P(=O)_2$—$R_e$, —$S(=O)_2OR_e$, —$P(=O)_2OR_e$, —$U_1$—$NR_bR_c$, —$U_1$—$N(R_d)$—$U_2$—$NR_bR_c$, —$U_1$—$NR_d$—$U_2$—$R_b$, —$NR_bP(=O)_2R_e$, —$P(=O)_2NR_bR_e$, —$C(=O)OR_e$, —$C(=O)R_a$, —OC(=O)$R_a$, —$NR_dP(=O)_2NR_bR_c$, —$R_bP(=O)_2R_e$, —$U_1$-aryl, —$U_1$-heteroaryl, —$U_1$-cycloalkyl, —$U_1$-heterocyclo, —$U_1$-arylene-$R_e$, —$U_1$-heteroarylene-$R_e$, —$U_1$—cycloalkylene-$R_e$, and/or —$U_1$-heterocyclene-$R_e$,
  wherein, in group (i),
  (ii) —$U_1$— and —$U_2$— are each independently a single bond, —$U^3$—$S(O)_t$—$U^4$—, $U^3$—$C(O)$—$U^4$—, —U³—C(S)—U⁴—, —U³—O—U⁴—, —U³—S—U⁴—, —U³—O—C(O)—U⁴—, —U³—C(O)—O—U⁴—, or —U³—C(=NR_g)—U⁴—;

wherein, (iii) U³ and U⁴ are each independently a single bond, alkylene, alkenylene, or alkynylene;

wherein, in group (i), (iv) $R_a$, $R_b$, $R_c$, $R_d$, and $R_e$ are each independently hydrogen, alkyl, alkenyl, alkynyl, cycloalkyl, aryl, heterocyclo, or heteroaryl, each of which is unsubstituted or substituted with one to four groups $R_f$, except $R_e$ is not hydrogen; or $R_{b\ and\ Rc}$ may be taken together to form a 3- to 8-membered saturated or unsaturated ring together with the atoms to which they are attached, which ring is unsubstituted or substituted with one to four groups listed below for $R_f$; or $R_b$ and $R_c$ together with the nitrogen atom to which they are attached may combine to form a group —N=C $R_g R_h$, where $R_g$ and $R_h$ are each independently hydrogen, alkyl, or alkyl substituted with a group $R_f$; and;

wherein, (v) $R_f$ is at each occurrence independently selected from alkyl, halogen, cyano, hydroxy, —O(alkyl), SH, —S(alkyl), amino, alkylamino, haloalkyl, haloalkoxy, or a lower alkyl substituted with one to two of halogen, cyano, hydroxy, —O(alkyl), SH, —S(alkyl), amino, alkylamino, haloalkyl, and/or haloalkoxy, and wherein, (vi) t is 0, 1 or 2.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. A substituted alkenyl refers to an alkenyl having one or more substituents (preferably 1 to 3 substituents, even more preferably 1 to 2 substituents), selected from those defined above for substituted alkyl.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. A substituted alkynyl refers to an alkynyl having one or more substituents (preferably 1 to 4 substituents, even more preferably 1 to 2 substituents), selected from those defined above for substituted alkyl.

When the term "alkyl" is used as a suffix with another group, such as in (aryl)alkyl or arylalkyl, this conjunction is meant to refer to a substituted alkyl group wherein at least one of the substituents is the specifically named group in the conjunction. For example, (aryl)alkyl refers to a substituted alkyl group as defined above wherein at least one of the alkyl substituents is an aryl, such as benzyl. However, in groups designated —O(alkyl) and —S(alkyl), it should be understood that the points of attachment in these instance are to the oxygen and sulfur atoms, respectively.

Where alkyl groups as defined are divalent, i.e., with two single bonds for attachment to two other groups, they are termed "alkylene" groups. Similarly, where alkenyl groups as defined above and alkynyl groups as defined above, respectively, are divalent radicals having single bonds for attachment to two other groups, they are termed "alkenylene groups" and "alkynylene groups" respectively. Examples of alkylene, alkenylene and alkynylene groups include:

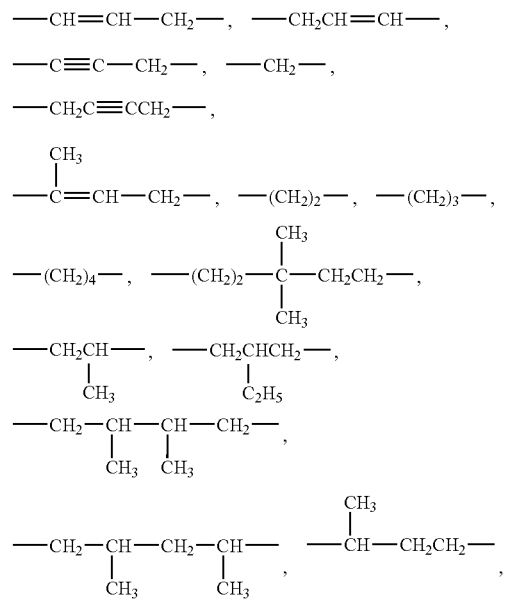

and the like. Alkylene groups may be optionally independently substituted as valence allows with one or more groups as defined for substituted alkyl groups. Thus, for example, a substituted alkylene group would include

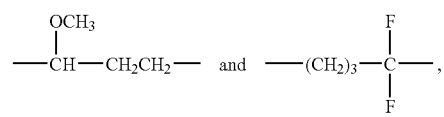

and so forth.

The term "cycloalkyl" as used herein by itself or as part of another group refers to optionally-substituted saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The further rings of multi-ring cycloalkyls may be either fused, bridged and/or joined through one or more spiro union. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cycloheptenyl, cyclooctenyl, cyclohexadienyl, cycloheptadienyl,

-continued

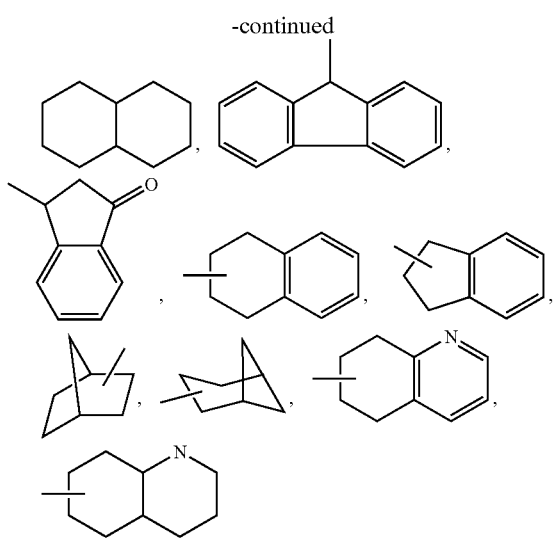

and the like.

Each reference to a cycloalkyl is intended to include both substituted and unsubstituted cycloalkyl groups as defined immediately below, unless reference is made to a particular selection of substituents to be made for the cycloalkyl (e.g., as with $R^{10}$ in the claims, and as below, wherein cycloalkyl is substituted with one or more groups $R_f$.) When no particular selection is recited, the optional substituents for the cycloalkyl groups may be selected from the following:

(i) halogen (e.g., a single halo substituent or multiple halo substitutents forming, in the latter case, groups such as a perfluoroalkyl group or an alkyl group bearing $Cl_3$ or $CF_3$), haloalkoxy, cyano, nitro, oxo (=O), —$OR_a$, —$SR_a$, —$S(=O)R_c$, —$S(=O)_2R_c$, —$S(=O)_3H$, —$P(=O)_2$—$R_e$, —$S(=O)_2OR_e$, —$P(=O)_2OR_e$, —$U_1$—$NR_bR_c$, —$U_1$—$N(R_d)$—$U_2$—$NR_bR_c$, —$U_1$—$NR_d$—$U_2$—$R_b$, —$NR_bP(=O)_2R_e$, —$P(=O)_2NR_bR_c$, —$C(=O)OR_c$, —$C(=O)R_a$, —$OC(=O)R_a$, —$NR_dP(=O)_2NR_bR_c$, —$R_bP(=O)_2R_e$, and/or —$U_1$—$R_e$, and/or (ii) —$U_1$-alkyl, —$U_1$-alkenyl, or —$U_1$-alkynyl wherein the alkyl, alkenyl, and alkynyl are substituted with one or more (preferably 1 to 3) groups recited in (i), wherein, in groups (i) and (ii), (iii) —$U_1$— and —$U_2$— are each independently a single bond, —$U^3$—$S(O)_t$—$U^4$—, —$U^3$—$C(O)$—$U^4$—, —$U^3$—$C(S)$—$U^4$—, —$U^3$—$O$—$U^4$—, —$U^3$—$S$—$U^4$—, —$U^3$—$O$—$C(O)$—$U^4$—, —$U^3$—$C(O)$—$O$—$U^4$—, or —$U^3$—$C(=NR_g)$—$U^4$—;

wherein, in group (iii), (iv) $U^3$ and $U^4$ are each independently a single bond, alkylene, alkenylene, or alkynylene;

wherein, (v) $R_a$, $R_b$, $R_c$, $R_d$, and $R_e$ are each independently hydrogen, alkyl, alkenyl, alkynyl, cycloalkyl, aryl, heterocyclo, or heteroaryl, each of which is unsubstituted or substituted with one or more groups $R_f$, except $R_e$ is not hydrogen; or $R_b$ and $R_c$ may be taken together to form a 3- to 8-membered saturated or unsaturated ring together with the atoms to which they are attached, which ring is unsubstituted or substituted with one or more groups listed below for $R_f$, or $R_b$ and $R_c$ together with the nitrogen atom to which they are attached may combine to form a group —$N=C R_gR_h$, where $R_g$ and $R_h$ are each independently hydrogen, alkyl, or alkyl substituted with a group $R_f$; and;

wherein, (vi) $R_f$ is at each occurrence independently selected from alkyl, halogen, cyano, hydroxy, —O(alkyl), SH, —S(alkyl), amino, alkylamino, haloalkyl, haloalkoxy, or a lower alkyl substituted with one to two of halogen, cyano, hydroxy, —O(alkyl), SH, —S(alkyl), amino, alkylamino, haloalkyl, and/or haloalkoxy, and wherein, (vii) t is 0, 1 or 2.

When the suffix "ene" is used in conjunction with a cyclic group, this is intended to mean the cyclic group as defined herein having two single bonds as points of attachment to other groups. Thus, for example, the term "cycloalkylene" as employed herein refers to a "cycloalkyl" group as defined above which is a linking group such as

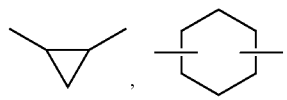

and the like.

The term "alkoxy" refers to an alkyl or substituted alkyl group as defined above bonded through an oxygen atom (—O—), i.e., the group —$OR_i$, wherein $R_i$ is alkyl or substituted alkyl.

The term "alkylthio" refers to an alkyl or substituted alkyl group as defined above bonded through a sulfur atom (—S—), i.e., the group —$SR_i$, wherein $R_i$ is alkyl or substituted alkyl.

The term "acyl" refers to a carbonyl group linked to an alkyl radical, more particularly, the group $C(=O)R_j$, wherein $R_j$ can be selected from alkyl, alkenyl, substituted alkyl, or substituted alkenyl, as defined herein.

The term "alkoxycarbonyl" refers to a carboxy group

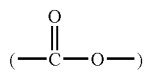

linked to an alkyl radical ($CO_2R_j$), wherein $R_j$ is as defined above for acyl. When the designation "$CO_2$" is used herein, this is intended to refer to the group

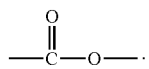

The term "alkylamino" refers to amino groups wherein one or both of the hydrogen atoms is replaced with an alkyl group, i e., $NR_kR_l$, wherein one of $R_k$ and $R_l$ is hydrogen and the other is alkyl, or both $R_k$ and $R_l$ are alkyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The terms "ar" or "aryl" as used herein by itself or as part of another group refer to optionally-substituted aromatic homocyclic (i.e., hydrocarbon) monocyclic, bicyclic or tricyclic aromatic groups containing 6 to 14 carbons in the ring portion [such as phenyl, biphenyl, naphthyl (including 1-naphthyl and 2-naphthyl) and antracenyl], and may optionally include one to three additional rings (either cycloalkyl, heterocyclo or heteroaryl) fused thereto. Examples include:

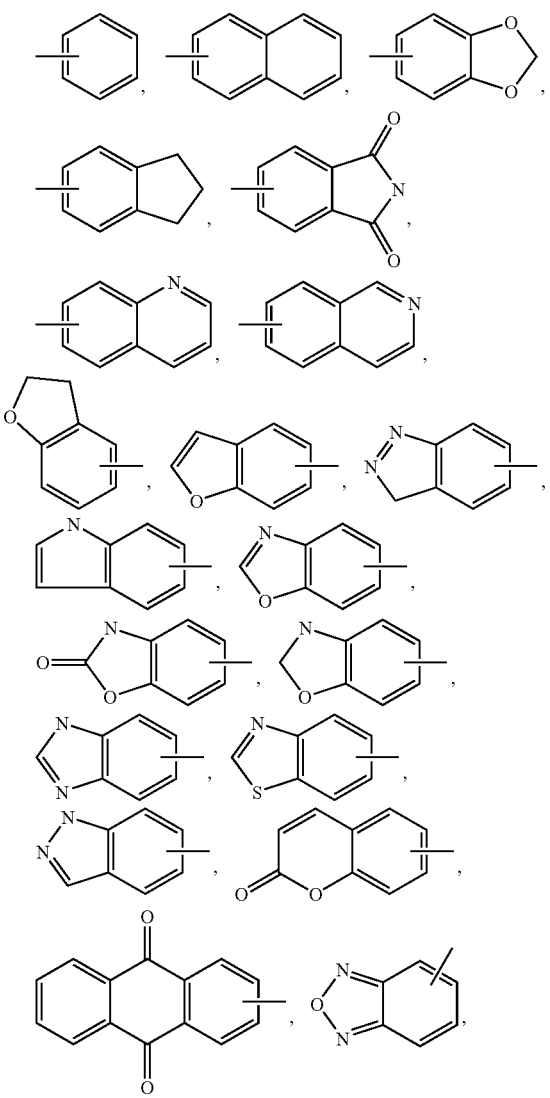

and the like.

Each reference to an aryl is intended to include both substituted and unsubstituted aryl groups as defined herein, unless reference is made to a particular selection of substituents to be made for the aryl (e.g., as when aryl is substituted with one or more groups $R_f$, above, and as with $R_{10}$ in the claims). When no particular selection is recited, the optional substituents for the aryl groups may be selected from those recited above, as valence allows, for cycloalkyl groups.

The term "heteroaryl" as used herein by itself or as part of another group refers to optionally-substituted monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

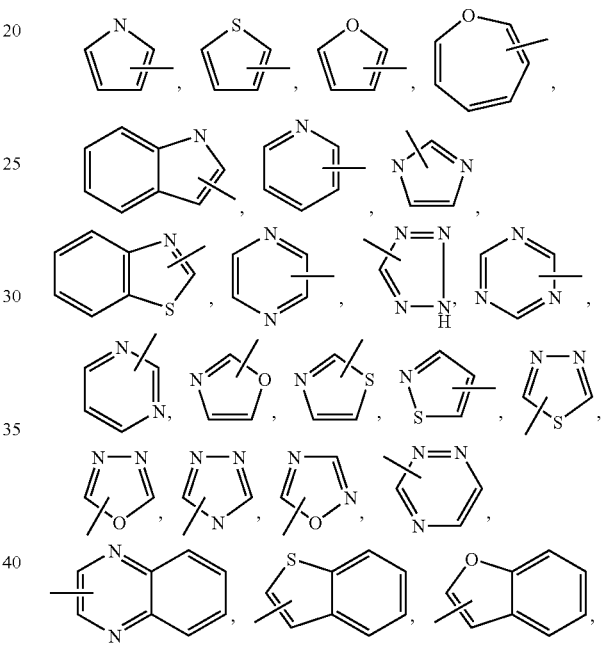

and the like.

In compounds of formula (I), preferred heteroaryl groups include

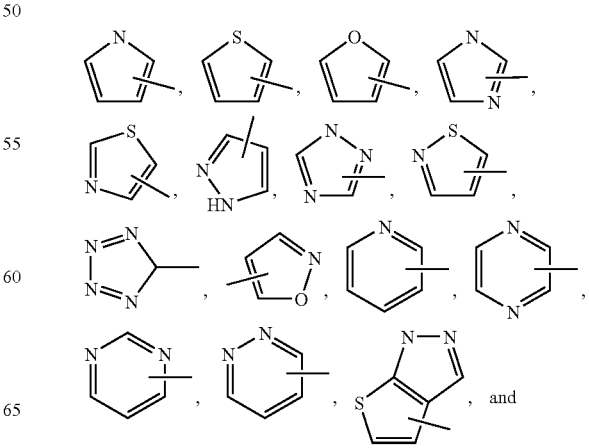

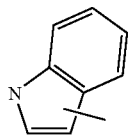

which optionally may be substituted at any available carbon or nitrogen atom.

Each reference to a heteroaryl is intended to include both substituted and unsubstituted heteroaryl groups as defined herein, unless reference is made to a particular selection of substituents to be made for the heteroaryl (e.g., as when heteroaryl is substituted with one or more groups $R_f$, above, and as with $R_{10}$ in the claims). When no particular selection is recited, the optional substituents for the heteroaryl groups may be selected from those recited above, as valence allows, for cycloalkyl groups.

The terms "heterocyclic" or "heterocyclo" as used herein by itself or as part of another group refer to non-aromatic, optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be fused, bridged and/or joined through one or more spiro unions.

Exemplary heterocyclic groups include oxetanyl, imidazolinyl, oxazolidinyl, isoxazolinyl, thiazolidinyl, isothiazolidinyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

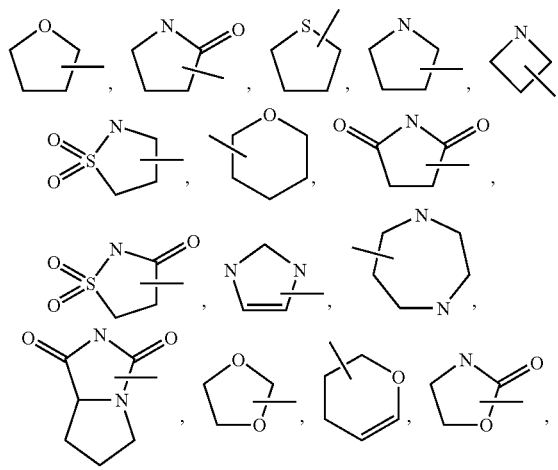

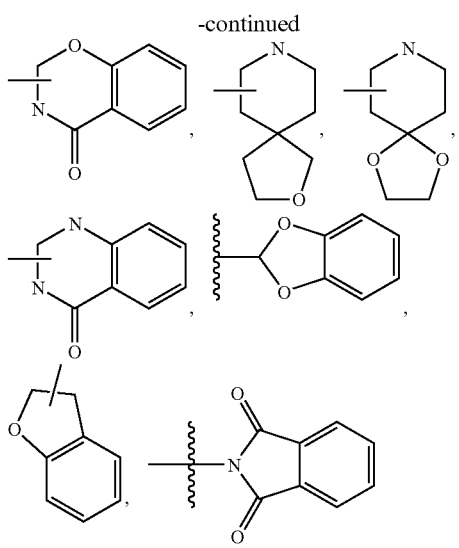

and the like, which optionally may be substituted.

Each reference to a heterocyclo is intended to include both substituted and unsubstituted heterocyclo groups as defined herein, unless reference is made to a particular selection of substituents to be made for the heterocyclo (e.g., as when heterocyclo is substituted with one or more groups $R_f$, above, and as with $R_{10}$ in the claims). When no particular selection is recited, the optional substituents for the heterocyclo groups may be selected from those recited above, as valence allows, for cycloalkyl groups.

Preferred heterocyclo groups in compounds of formula (I) include

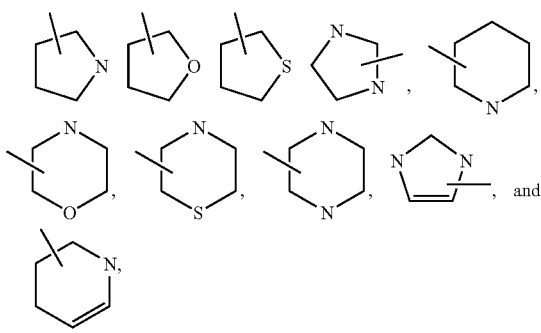

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated.

Unless otherwise indicated, when reference is made to a specifically-named aryl (e.g., phenyl), cycloalkyl (e.g, cyclohexyl), heterocyclo (e.g., pyrrolidinyl) or heteroaryl (e.g., imidazolyl), unless otherwise specifically indicated, the reference is intended to include rings having 0 to 3, preferably 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

In compounds of formula (I), the group —Y—B is defined as being attached to the phenyl or pyridyl ring in the meta or para position, which means compounds having the formulae,

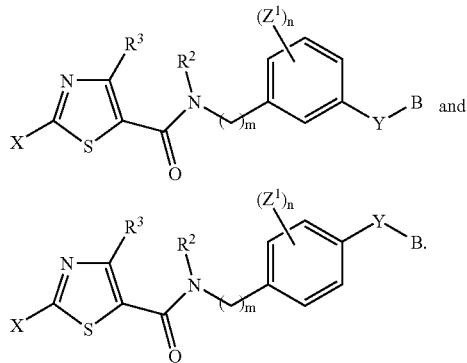

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds. One skilled in the field may make the appropriate selections for B and X to provide stable compounds.

PREFERRED COMPOUNDS

Preferred compounds of the invention include compounds having the formula (I*),

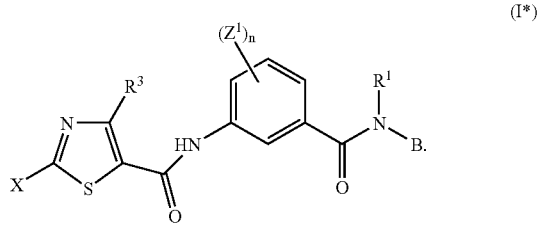

enantiomers, diastereomers, pharmaceutically-acceptable salts, prodrugs, and solvates thereof, wherein:
$R^1$ is hydrogen or alkyl (more preferably $C_{1-4}$alkyl);
B is
  (a) hydrogen, or
  (b) alkyl (more preferably lower alkyl), cycloalkyl (more preferably $C_{3-7}$cycloalkyl), or heteroaryl (more preferably five to six membered heteroaryl rings) any of which may be optionally substituted with $Z^{1b}$, $Z^{2b}$ and up to two $Z^{3b}$;

$R^3$ is hydrogen, alkyl (more preferably methyl), haloalkyl (more preferably perfluoromethyl), alkoxy (more preferably methoxy), (alkoxy)alkyl, hydroxy, (hydroxy)alkyl, halogen, cyano, or —$NR^6R^7$ where $R^6$ and $R^7$ are independently hydrogen or optionally-substituted alkyl;

X is

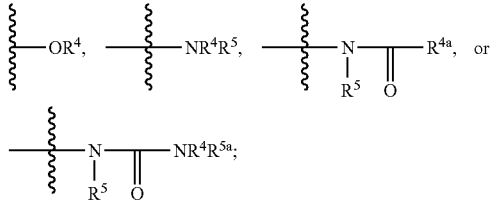

$R^4$ and $R^{5a}$ is
  (a) hydrogen, or
  (b) alkyl, cycloalkyl, alkenyl, aryl, heteroaryl, or heterocyclo any of which may be optionally substituted with $Z^{1d}$, $Z^{2d}$ and up to two $Z^{3d}$ $R^{4a}$ is
  (a) hydrogen, or
  (b) alkyl, cycloalkyl, alkenyl, alkoxy, aryl, heteroaryl, or heterocyclo, any of which may be optionally substituted with $Z^{1d}$, $Z^{2d}$ and up to two $Z^{3d}$;

$R^5$ is hydrogen or optionally-substituted alkyl;

$Z^1$, $Z^{1b}$, $Z^{2b}$, and $Z^{3b}$ are selected from halo, alkyl, haloalkyl, haloalkoxy, cycloalkyl, (cycloalkyl)alkyl, (aryl)alkyl, (heteroaryl)alkyl, cyano, $NR^{12}R^{13}$ ($NR^{12}R^{13}$)alkyl, $OR^{10}$, $SR^{10}$;

$R^{10}$, $R^{12}$, and $R^{13}$ are hydrogen or alkyl, and n is 0, 1 or 2.

Preferred compounds also include compounds of formula (I), including compounds of formula (I*), as immediately defined above, wherein B is hydrogen, alkyl, or cycloalkyl (more preferably methyl, ethyl or cyclopropyl), $R_3$ is hydrogen, $Z^1$ is alkyl (more preferably methyl), and n is 1. In compounds of formula (I*), n is preferably 0 or 1, even more preferably 1 wherein $Z^1$ is in the ortho position.

In compounds of formula (I), including compounds of formula (I*), X is preferably

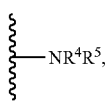

and more preferably X is NH($C_{1-6}$alkyl).

Preferred compounds of formula (I) and formula (I*) include compounds wherein $R^4$ is alkyl (more preferably $C_{1-6}$alkyl), (alkoxy)alkyl, cycloalkyl (more preferably cyclopropyl, cyclobutyl, cyclopentyl and cyclohexyl), aryl (more preferably phenyl), (aryl)alkyl (more preferably benzyl), heterocyclo (more preferably five to six membered rings such as pyrrolidinyl, piperidinyl, or morpholinyl), (heterocyclo)alkyl, heteroaryl (more preferably five to six-membered rings such as pyridyl), and (heteroaryl)alkyl (more preferably containing five to six-membered rings such as (pyridyl)methyl), wherein each $R^4$ group in turn is optionally independently substituted with one to two of alkyl (preferably $C_{1-4}$alkyl), alkoxy (more preferably $C_{1-4}$alkoxy), halogen, cyano, haloalkyl (more preferably trifluoromethyl), and/or haloalkoxy (more preferably trifluoromethoxy).

Also preferred compounds include compounds having the formula,

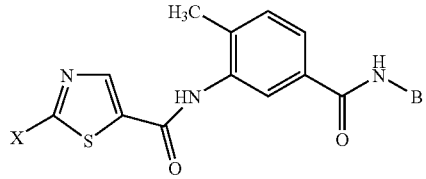
(Ia*)

and pharmaceutically-acceptable salts, prodrugs, and solvates thereof, wherein

B and X are selected from groups as recited above for compounds of formula (I*).

Most preferred compounds include compounds of formula (Ia*), wherein

B is hydrogen, alkyl (more preferably methyl, ethyl or propyl), cycloalkyl (more preferably cyclopropyl), or heteroaryl (more preferably pyrazolyl or isoxazolyl optionally substituted with one or more alkyl);

X is $NR^4R^5$;

$R^4$ is alkyl (more preferably methyl, ethyl, iso-propyl, n-propyl, sec-butyl, iso-butyl, or n-butyl), (alkoxy)alkyl, cycloalkyl (more preferably cyclopropyl, cyclobutyl, cyclopentyl, or cyclohexyl), aryl (more preferably phenyl), (aryl)alkyl (more preferably benzyl), or (heteroaryl)alkyl (more preferably pyridylmethyl), wherein each $R^4$ group in turn is optionally independently substituted with zero to two of alkyl, alkyoxy, halo, cyano, haloalkyl, and/or haloalkoxy; and $R_5$ is hydrogen;

or $R_4$ and $R_5$ may be taken together to form a heterocyclo ring (more preferably pyrrolyl, morpholinyl, piperidinyl, or piperazinyl), said heterocyclo ring being independently optionally substituted with or more alkyl, alkyoxy, halo, cyano, haloalkyl, and/or haloalkoxy.

Compounds of the following formula II are useful as intermediates to prepare compounds of formula I:

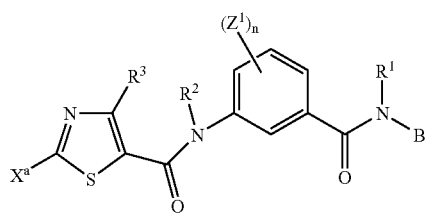
II wherein $R^1$, $R^2$, $R^3$, B, $Z^1$ and n are as defined in the Summary of Invention for compounds of formula I, and more preferably wherein such groups are selected from the description of preferred groups as defined above; and $X^a$ is halogen, more preferably chlorine or bromine.

Compounds of the following formula III are also useful as intermediates to compounds of formula I:

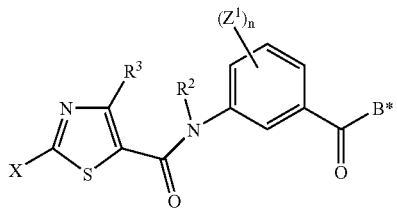
III wherein $R^1$, $R^2$, $R^3$, X, $Z^1$, and n are as defined in the Summary of Invention for compounds of formula I, and more preferably wherein such groups are selected from the description of preferred groups as defined above; and B* is OH or $OR^{10}$ where $R^{10}$ is as defined above in the description of compounds of formula I.

UTILITY

The compounds of the invention are selective inhibitors of p38 kinase, and in particular, isoforms p38α and p38β. Accordingly, compounds of formula (I) have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its sypmtoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited.

In view of their activity as inhibitors of p-38α/β kinase, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to infectious diseases such as sepsis, septic shock, Shigellosis, and *Heliobacter Pylori*.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS<ARC or malignancy, and herpes.

The inventive compounds also may be used to treat angiogenic disorders including solid tumors, ocular neovasculization, and infantile haemangiomas.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is modulated by p38 kinase activity.

The present invention thus provides methods for treating such conditions, comprising administering to a subject in need thereof an effective amount of at least one compound of Formula (I), or a pharmaceutically-acceptable salt, hydrate, or prodrug thereof. The methods of treating p38 kinase-associated conditions may comprise administering compounds of Formula (I) alone or in combination with each other and/or other suitable therapeutic agents such as anti-inflammatory drugs, antibiotics, anti-viral agents, antioxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or other NF-κB inhibitors (such calphostin, CSAIDs, and quinoxalines as disclosed in U.S. Pat. No. 4,200,750); corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan.

Examples of suitable antibiotics with which the inventive compounds may be used include β-lactams (e.g, penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196–2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epothilones, ixabepilone, cisplatin, and carboplatin, including compounds claimed in U.S. Pat. Nos. 6,605,599, and 6,262,094, incorporated herein by reference.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$, and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

Additionally, the inventive compounds may be used in combination with lipid profile modulators and antiatherosclerotic agents including HMG-CoA reductase inhibitors (e.g, pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal $Na^+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds within the scope of formula (I) may be tested for activity as inhibitors of p38α/β enzymes and TNF-α using the assays described below, or variations thereof that are within the level ordinary skill in the art. Compounds described in the examples herein have been tested and shown activity as inhibitors of p38α/β enzymes and TNF-α.

BIOLOGICAL ASSAYS

Generation of p38 Kinases cDNAs of human p38α, β and γ isozymes are cloned by PCR. These cDNAs can be subcloned in the pGEX expression vector (Pharmacia). GST-p38 fusion protein is expressed in *E. Coli* and purified from bacterial pellets by affinity chromatography using glutathione agarose. p38 fusion protein is activated by incubating with constitutively active MKK6. Active p38 is separated from MKK6 by affinity chromatography. Constitutively active MKK6 is generated according to Raingeaud et al. [*Mol. Cell. Biol.,* 1247–1255 (1996)].

TNF-α Production by LPS-Stimulated PBMCs

Heparinized human whole blood is obtained from healthy volunteers. Peripheral blood mononuclear cells (PBMCs) are purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension is incubated with 50 ul of test compound (4× concentration in assay medium containing 0.2% DMSO) in 96-well tissue culture plates for 5 minutes at RT. 100 ul of LPS (200 ng/ml stock) is then added to the cell suspension and the plate is incubated for 6 hours at 37° C. Following incubation, the culture medium is collected and stored at −20° C. TNF-α concentration in the medium is quantified using a standard ELISA kit (Pharmingen-San Diego, Calif.). Concentrations of TNF-α and $IC_{50}$ values for test compounds (concentration of compound that inhibited LPS-stimulated TNF-α production by 50%) are calculated by linear regression analysis.

p38 Assay

The assays are performed in V-bottomed 96-well plates. The final assay volume is 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 is pre-incubated with test compounds for 10 min. prior to initiation of reaction with substrates. The reaction is incubated at 25° C. for 45 min. and terminated by adding 5 μl of 0.5 M EDTA to each sample. The reaction mixture is aspirated onto a pre-wet filtermat using a Skatron Micro96 Cell Harvester (Skatron, Inc.), then washed with PBS. The filtermat is then dried in a microwave oven for 1 min., treated with MeltiLex A scintillation wax (Wallac), and counted on a Microbeta scintillation counter Model 1450 (Wallac). Inhibition data are analyzed by nonlinear least-squares regression using Prizm (GraphPadSoftware). The final concentration of reagents in the assays are ATP, 1 μM; [γ-$^{33}$P]ATP, 3 nM,; MBP (Sigma, #M1891), 2 μg/well; p38, 10 nM; and DMSO, 0.3%.

TNF-α Production by LPS-Stimulated Mice

Mice (Balb/c female, 6–8 weeks of age, Harlan Labs; n=8/treatment group) are injected intraperitoneally with 50 ug/kg lipopolysaccharide (LPS; *E coli* strain 0111:B4, Sigma) suspended in sterile saline. Ninety minutes later, mice are sedated by $CO_2$:$O_2$ inhalation and a blood sample was obtained. Serum is separated and analyzed for TNF-alpha concentrations by commercial ELISA assay per the manufacturer's instructions (R&D Systems, Minneapolis, Minn.).

Test compounds are administered orally at various times before LPS injection. The compounds are dosed either as suspensions or as solutions in various vehicles or solubilizing agents.

ABBREVIATIONS

For ease of reference, the following abbreviations are employed herein, including the methods of preparation and Examples that follow:

Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DMF=dimethyl formamide
DMF-DMA=N,N-dimethylformamide dimethyl acetal
DMSO=dimethyl sulfoxide
DPPF=1,1'-bis(diphenylphosphino)ferrocene
HATU=O-benzotriazol-1-yl0 N,N,N',N'-tetramethyluronium hexafluorphosphate
LDA=lithium di-isopropyl amide
TEA=triethylamine
TFA=trifluoroacetic acid
THF=tetrahydrofuran
KOH=potassium hydroxide
$K_2CO_3$=potassium carbonate
KOtBu=potassium t-butoxide
$POCl_3$=phosphorous oxychloride
EDC or EDCI=3-ethyl-3'-(dimethylamino)propyl-carbodiimide
DIPEA=diisopropylethylamine
HOBt=1-hydroxybenzotriazole hydrate
NBS=N-bromosuccinamide
NMP=N-methyl-2-pyrrolidinone
NaH=sodium hydride
NaOH=sodium hydroxide
$Na_2S_2O_3$=sodium thiosulfate
Pd=palladium
Pd—C or Pd/C=palladium on carbon
min=minute(s)
L=liter
mL=milliliter
μL=microliter
g=gram(s)
mg=milligram(s)
mol=moles
mmol=millimole(s)
meq=milliequivalent RT or rt=room temperature
RBF=round bottom flask
ret. t.=HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point In the Examples, "HPLC Condition A" refers to YMC S5 ODS 4.6×50 mm Ballistic column, 4 mL/min flow rate, 4 min linear gradient elution (Start solvent % B=0; Final solvent % B=100), solvent A=10% MeOH/90% $H_2O$/0.2% $H_3PO_4$.

"HPLC condition B" refers to Phenomenex Primesphere 4.6×50 mm, 4 mL/min flow rate, 2 min linear gradient elution (Start solvent % B=0; Final solvent % B=100), solvent A=10% MeOH/90% $H_2O$/0.2% TFA, solvent B=90% MeOH/10% $H_2O$/0.2% TFA.

METHODS OF PREPARATION

Compounds of Formula (I) may be prepared according to the following Schemes and the knowledge of one skilled in the art. Solvents, temperatures, pressures, and other reaction conditions may readily be selected by one of ordinary skill in the art. In each of Schemes 1–9, it should be understood that the aromatic ring to which the group —Y—B is attached may be a phenyl or pyridyl ring.

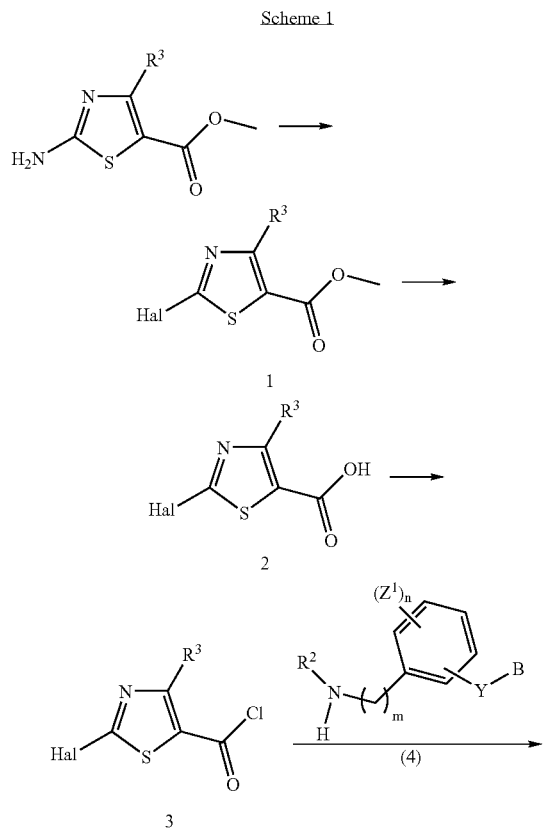

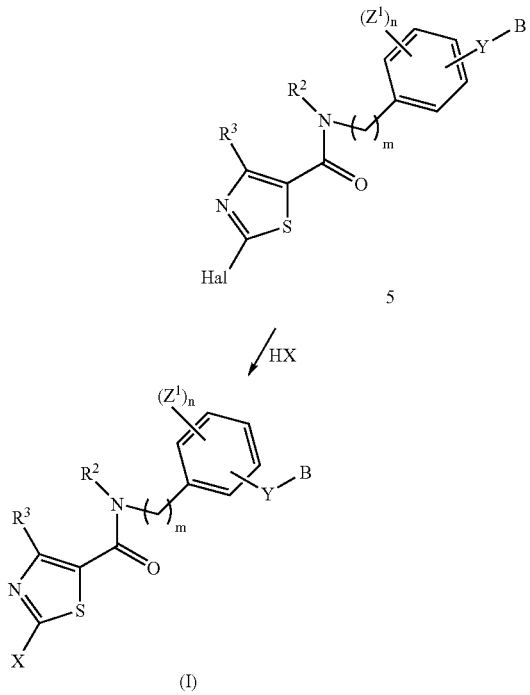

Compounds of Formula (I) can be prepared as outlined in Scheme 1, by reacting a 2-amino thiazole, such as methyl 2-amino-4-methyl-thiazole carboxylate, with t-Bu-nitrite and a halide source, such as $CuBr_2$, in a suitable solvent to produce compound (1). Reacting compound (1) under standard saponification conditions, such as aqueous hydroxide, produces compound (2). Compound (2) can be reacted with halogenating agents, such as $SOCl_2$, to produce compound (3). Reacting compound (3) with a base such as DIPEA and compounds of formula (4) produces compound (5). Reaction of compound (5) with XH, wherein X is as defined herein, in an appropriate solvent produces compounds of Formula (Ia). Compounds having the formula (4) in Scheme 1 can be produced as shown in Schemes 2 and 3.

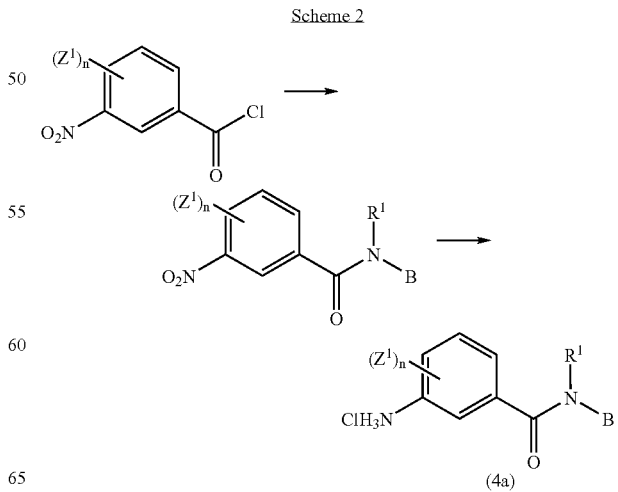

Compounds (4a) can be prepared as outlined in Scheme 2 by 1) reacting a 3-nitro-benzoyl chloride and an amine NHBR[1] in CH$_2$Cl$_2$ to give a nitro intermediate; 2) reacting the nitro intermediate under reducing conditions, such as hydrogen gas and a catalyst, in a solvent to produce an aniline intermediate; and 3) reacting that aniline intermediate with HCl to produce compounds (4a) as a hydrochloride salt.

Scheme 3

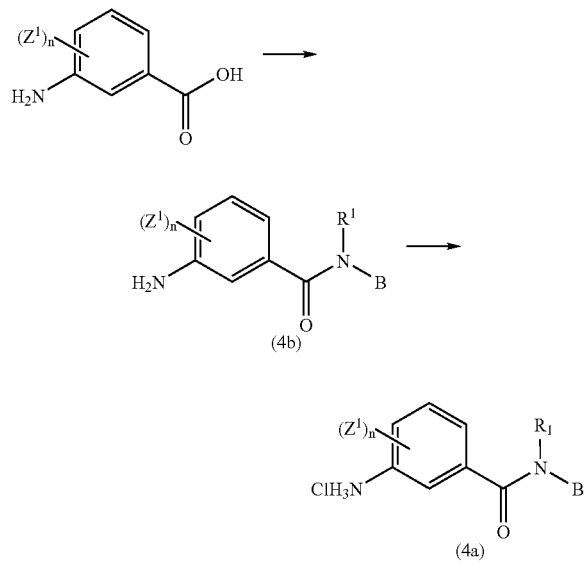

Alternatively to Scheme 2, compounds (4a) and compound (4b) can be prepared as outlined in Scheme 3, by reacting a 3-amino-benzoic acid and an amine NHBR[1] with a coupling agent, such as EDC/HOBt, in a suitable solvent to prepare aniline (4b) and reacting that aniline (4b) with HCl to produce compound (4a) as a hydrochloride salt.

Scheme 4a

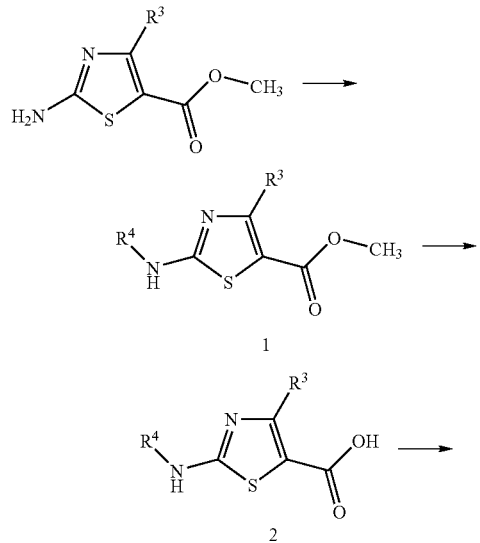

-continued

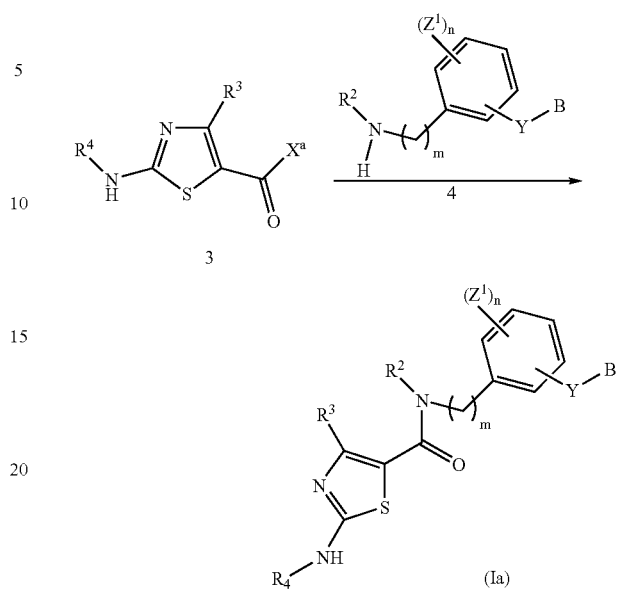

Compounds of Formula (Ia) (wherein X of formula I is —NHR[4]) can be prepared as outlined in Scheme 4a, by reacting a 2-amino-thiazole, such as methyl 2-amino-4-methyl-thiazole carboxylate, with various reagents to produce Compound (1). Reacting compound (1) under standard saponification conditions produces compound (2). Compound (2) can be reacted with an activating agent (such as SOCl$_2$, HATU or EDCi/HOBt) to produce compound (3). Reacting compound (3) with compound (4) produces compounds of Formula (Ia).

Scheme 4b

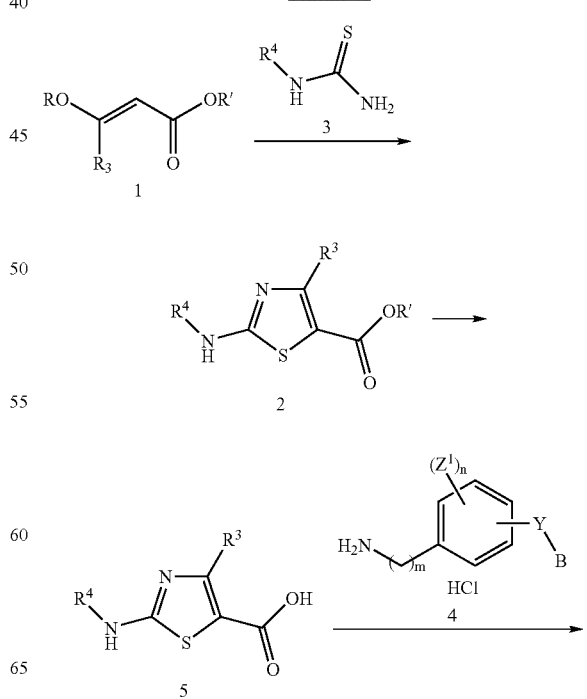

-continued

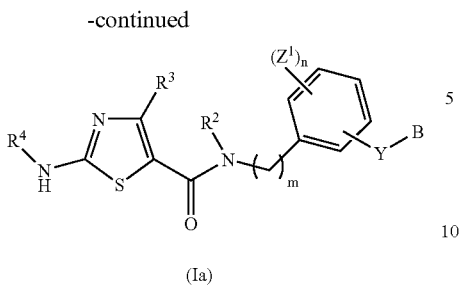

(Ia)

In Scheme 4b, alkyl β-alkoxyacetate (1), preferably ethyl β-ethoxyacrylate, is reacted by addition of a halogenating reagent, such as NBS, in the presence of compound (3), in an appropriate solvent or solvent system, to produce the ester (2). See, e.g., Zhao et al., *Tetrahedron Lett.*, Vol 42 (2001) at pp. 2101–2102. Reacting compound (2) under standard saponification conditions, upon treatment with base such as NaOH in an appropriate solvent or solvent system, produces compound (5). Compound (5) can be reacted with compound (4) as shown in other schemes (e.g., Schemes 4a, 5) to produce compounds of formula (Ia).

Scheme 5

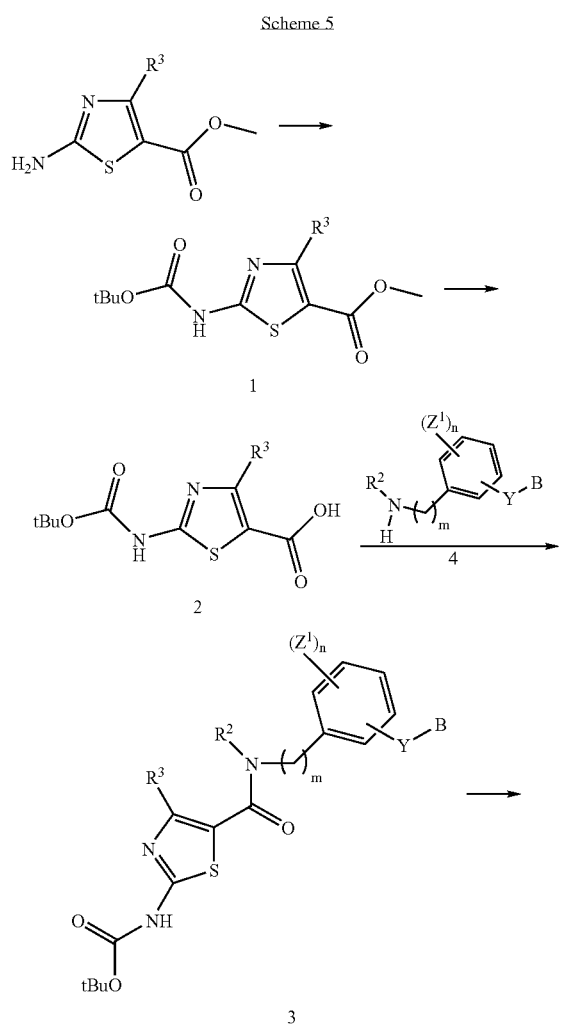

-continued

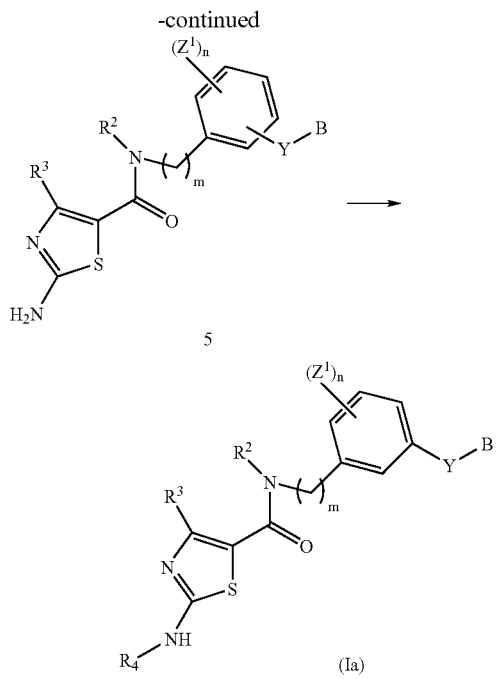

Compounds of Formula (Ia) where X is —NHR$^4$ can also be prepared as outlined in Scheme 5, by reacting a 2-aminothiazole, such as methyl 2-amino-4-methyl-thiazolecarboxylate, with various reagents, such as di-tert-Bu-dicarbonate, to produce compound (1). Reacting compound (1) under saponification conditions, such as aqueous hydroxide, produces compound (2). Compound (2) can be reacted with compound (4), e.g., in the presence of HATU/DIPEA or EDCI/HOBt, to produce compound (3). Compound (3) can be reacted with acid to produce compound (5) which can be reacted with various reagents to produce compounds of the Formula (Ia).

Scheme 6

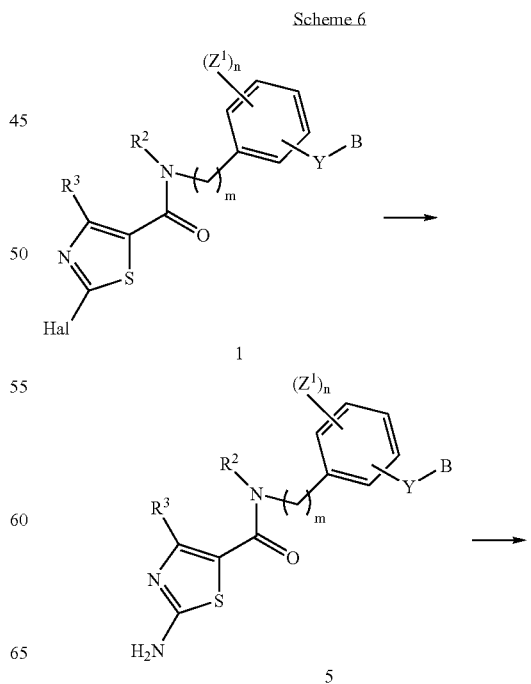

-continued

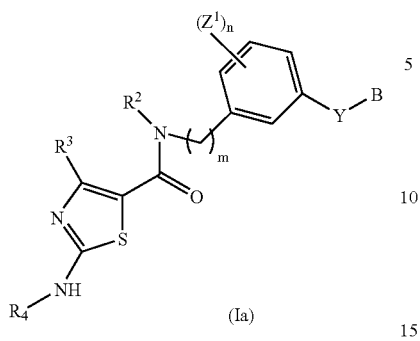

(Ia)

Alternatively, compounds of Formula (Ia) can be prepared as outlined in Scheme 6, by reacting compound (1) (Compound 5 of Scheme 1) with $NH_3$ to give compound (5). Reacting compound (5) with various reagents as in Scheme 5 produces compounds of the Formula (Ia). Reagents that may be included in the reaction of compound (5) to produce compounds of Formula (Ia) are alkyl and aryl halides, aldehydes, ketones, carboxylic acids, acid chlorides, sulfonyl chlorides, chloroformates, and isocyanates.

Scheme 7

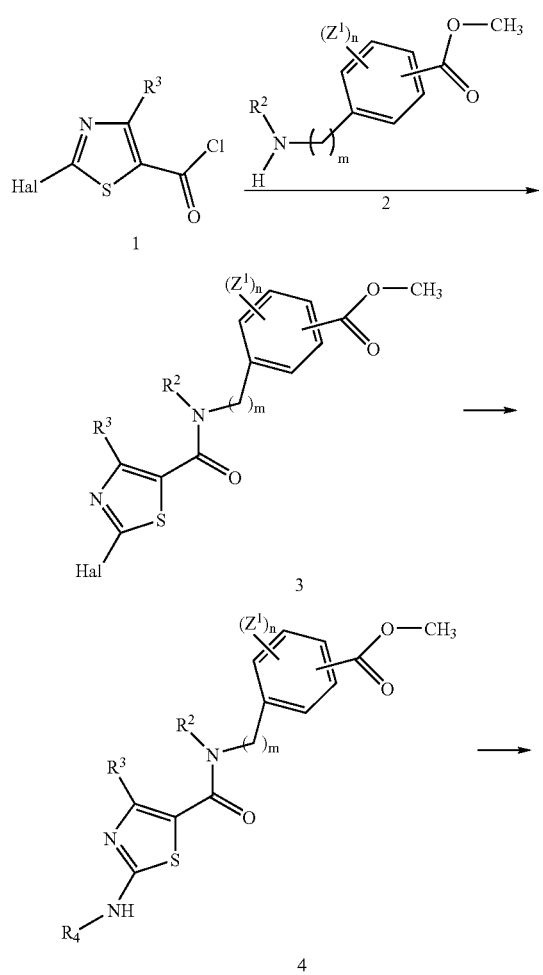

-continued

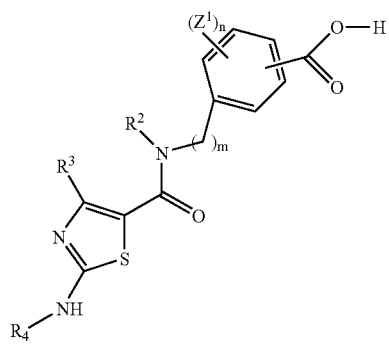

(Ib)

Alternatively, compounds of Formula (Ib) (Y is C(=O) $NR^1$) can be prepared as outlined in Scheme 7, by reacting compound (1) with compound (2) to produce compound (3). Reacting compound (3) with $H_2NR^4$ produces compound (4), and reacting compound (4) under standard saponification conditions produces compound (5). Reaction of compound (5) with various groups $NHBR^1$ produces compounds of Formula (Ib).

Scheme 8

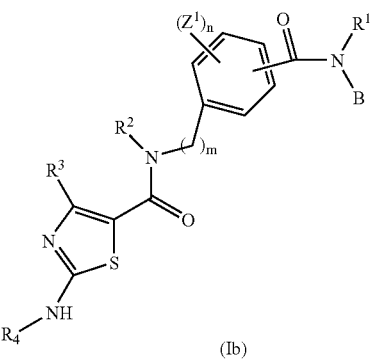

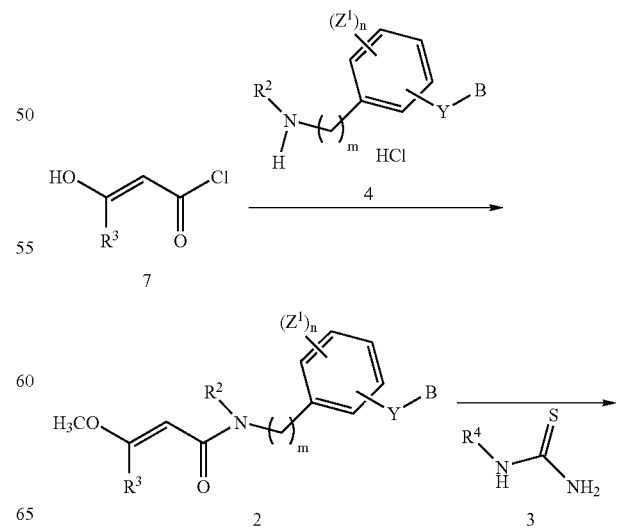

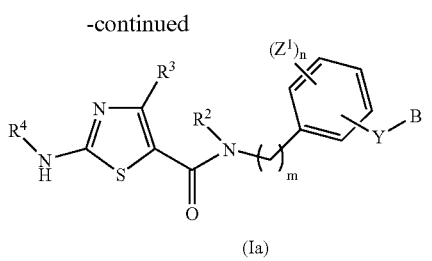

Compounds of formula (Ia) also can be prepared as shown in Scheme 8. 3-Methoxyacryloxyl chloride can be reacted with compounds of formula (4), in a suitable solvent, to produce compounds (2). Compounds (2) can be cyclized by addition of a halogenating reagent such as NBS in the presence of thiourea compound (3), in a suitable solvent or solvent mixture, to produce compounds of formula (Ia). Compound (3) is commercially available or can be produced by known methods, for example, by reaction of the appropriate amine in benzoylisothiocyanate in chloroform followed by treatment with base such as NaOH in solvent such as MeOH.

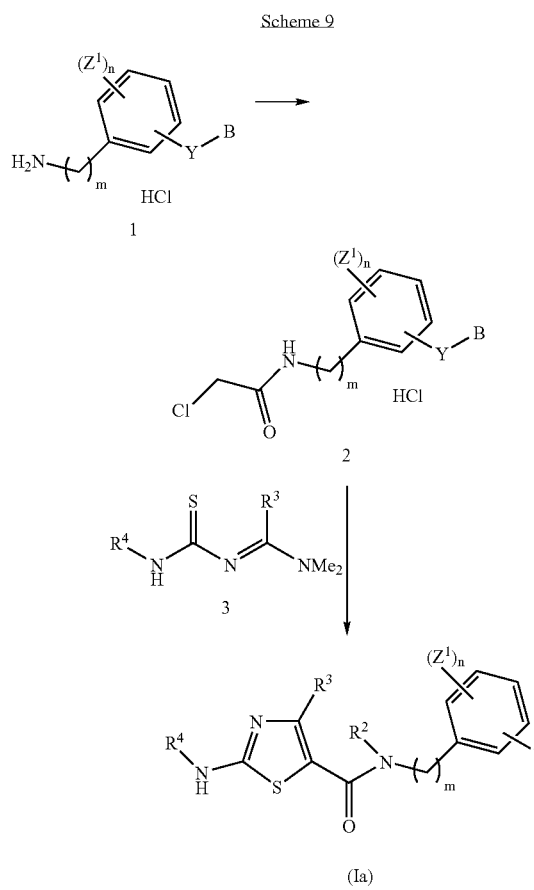

Alternatively compounds having formula (Ia) can be prepared as shown in Scheme 9. Compounds (1) can be treated with haloacetyl halide such as chloroacetyl chloride in the presence of base and a suitable solvent or solvent mixture to produce compounds (2). Reacting compound (2) with N,N-dimethylaminothiourea compound in a suitable solvent produces compounds of formula (Ia). Dimethylaminothiourea compounds (3) can be prepared by reacting thiourea compounds shown in Scheme 8a (i.e., compounds 3 of Scheme 8a), with DMF-DMA in an appropriate solvent such as EtOH.

EXAMPLES

The invention will now be further described by the following working examples, which are preferred embodiments of the invention. HPLC conditions were as set forth in the above Abbreviations. These examples are illustrative rather than limiting. There may be other embodiments that fall within the spirit and scope of the invention as defined by the appended claims.

Example 1

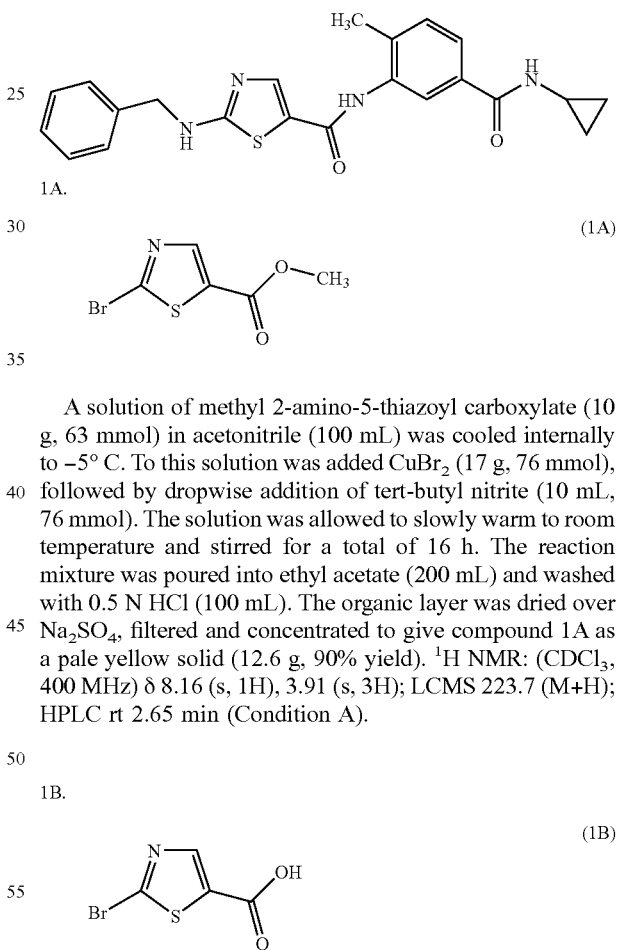

A solution of methyl 2-amino-5-thiazoyl carboxylate (10 g, 63 mmol) in acetonitrile (100 mL) was cooled internally to −5° C. To this solution was added $CuBr_2$ (17 g, 76 mmol), followed by dropwise addition of tert-butyl nitrite (10 mL, 76 mmol). The solution was allowed to slowly warm to room temperature and stirred for a total of 16 h. The reaction mixture was poured into ethyl acetate (200 mL) and washed with 0.5 N HCl (100 mL). The organic layer was dried over $Na_2SO_4$, filtered and concentrated to give compound 1A as a pale yellow solid (12.6 g, 90% yield). $^1$H NMR: (CDCl$_3$, 400 MHz) δ 8.16 (s, 1H), 3.91 (s, 3H); LCMS 223.7 (M+H); HPLC rt 2.65 min (Condition A).

1B.

To a solution of compound 1A (4.0 g, 18 mmol) in MeOH (20 mL) at 0° C. was added 10% NaOH (8 mL), and the reaction mixture was stirred for 1 h. The reaction was neutralized with 1N HCl, and the MeOH was removed on rotary evaporator. The precipitated solids were stirred vigorously for 2 h, filtered and washed with cold water to give compound 1B (3.2 g, 85% yield). LCMS 207.7 (M+H); HPLC rt 1.9 min.

1C.

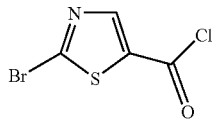

(1C)

To a solution of compound 1B (210 mg, 0.94 mmol) in ethyl acetate (3 mL) at room temp was added DMF (0.017 mL) and SOCl₂ (0.11 mL, 1.4 mmol), and the reaction mixture was stirred at reflux for 1 h. The reaction mixture was cooled and the volatiles removed on a rotary evaporator give compound 1C which was used without further purification in Step 1E, below.

1D.

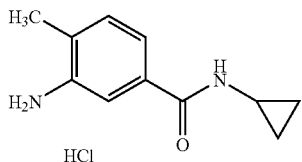

(1D)

A solution of 4-methyl-3-nitrobenzoyl chloride (69 g, 0.36 mol) in CH₂Cl₂ (400 mL) was cooled to 0° C., and then TEA (53 mL, 0.38 mol) was slowly added. A solution of cyclopropyl amine (25 g, 0.44 mol) in CH₂Cl₂ was added over 45 minutes while the internal reaction temperature was maintained below 5° C. The reaction was stirred for 1 h and then transferred to a separatory funnel with an additional 300 mL of CH₂Cl₂. This was then washed with 5% aq. HCl (500 mL) and brine (250 mL). The organic layer was dried over Na₂SO₄, filtered and concentrated. The crude solids were dissolved in hot EtOH (ca. 10 mL/g crude). Decolorizing carbon was added, and the reaction mixture was filtered through celite and concentrated again to produce a crude solid product. ¹H NMR: (CDCl₃, 400 MHz) δ 8.23 (d, J=1.7 Hz, 1H), 7.87 (dd, J=1.7, 7.9 Hz, 1H), 7.24 (d, J=8 Hz, 1H), 6.44 (br s, 1H), 2.85 (m, 1H), 2.57 (s, 3H), 0.82 (m, 2H), 0.59 (m, 2H); LCMS 221.1 (M+H); HPLC rt 2.71 min.

To a suspension of the above crude solid (90 g, 0.41 mol) in 1/1 EtOH/EtOAc (600 mL) was added an additional 200 mL of warm EtOH to aid with solubilizing the compound. To this solution was added 5% Pd—C (9 g, wet, Degussa type) and the mixture placed under hydrogen (45 psi) on a Parr shaker. Hydrogen was recharged at 10 minutes and 30 minutes. The reaction was shaken for 1 h and then filtered through celite. The filter was rinsed with EtOH (2×200 mL) and concentrated to an oil which solidified on standing. To a solution of the solidified oil (155 g, 0.81 mol) in absolute EtOH (1.55 L) at 0° C. was added HCl (70 mL, 12N) dropwise, while the internal temperature was maintained below 5° C. The solution was stirred at 0° C. for 4 h and filtered. The filter cake was washed with cold EtOH (2×125 mL). The solids were collected and dried under vacuum for 15 h to give compound 1D (162 g, 87% yield) as a white crystalline solid. ¹H NMR (DMSO-D₆, 400 MHz) δ 9.5 (br s, 2H), 8.27 (s, 1H), 7.53 (s, 1H), 7.40 (d, J=7.6 Hz, 1H), 7.11 (m, 1H), 2.60 (m, 1H), 2.13 (s, 3H), 0.45 (m, 2H), 0.34 (m, 2H); LCMS 191.1 (M+H); HPLC rt 0.58 min. YMC S5 ODS-A 4.6×50 mm, 4 min grad, 10% MeOH/H₂O to 90% MeOH/H₂O (0.2% H₃PO₄).

1E.

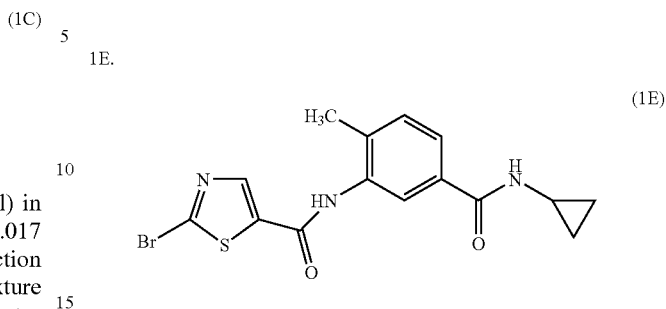

(1E)

To a solution of compound 1C (3.2 g, 14.4 mmol) and compound 1D (3.4 g, 15.1 mmol) in CH₂Cl₂ (100 mL) at 0° C. was added TEA (4.5 mL, 32 mmol,) and the reaction mixture was stirred for 2 h at 0° C., then at room temperature for 2 h. The reaction mixture was concentrated on a rotary evaporator. EtOH (100 mL) was added, and the reaction was stirred for 30 min followed by the addition of NaHCO₃ (sat. aq., 20 mL) and water (100 mL). Stirring was continued for 2 h and the solids were collected by vacuum filtration and washed with water to give compound 1E (4.1 g, 75% yield).

1F. Example 1

To a solution of compound 1E (20 mg, 0.05 mmol) in EtOH (1 mL) was added benzyl amine (0.023 mL, 0.21 mmol), and the reaction mixture was heated at 150° C. for 1 h. The reaction mixture was concentrated and the crude product precipitated from water to give Example 1 (17 mg, 79% yield). LCMS 407.2 (M+H); HPLC rt 3.21 min.

Examples 2–37

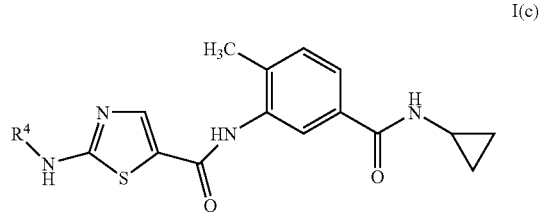

I(c)

Compounds having the above formula I(c), wherein R⁴ has the values set forth in Table 1, were prepared following the same or similar method described for Example 1, except in Step 1F, an appropriate amine was used in place of benzyl amine.

TABLE 1

| Example No. | R⁴ | Data MS/HPLC |
|---|---|---|
| 2 | H | 317.2, 1.83 |
| 3 | CH₃ | 331.1, 2.18 |
| 4 | —CH₂—CH₃ | 345.1, 2.42 |
| 5 | —(CH₂)₂CH₃ | 359.2, 2.72 |
| 6 | —CH—(CH₃)₂ | 359.2, 2.63 |
| 7 | CH₃<br>—CH—CH₂—CH₃ | 373.3, 3.50 |

TABLE 1-continued
| Example No. | R⁴ | Data MS/HPLC |
|---|---|---|
| 8 | 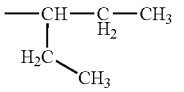 —CH—C—CH₃ with H₂C, CH₃, CH₃ | 387.2, 2.51 |
| 9 | 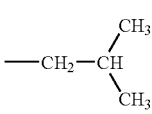 —CH₂—CH(CH₃)₂ | 373.2, 2.98 |
| 10 | 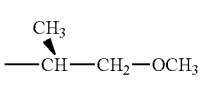 —CH(CH₃)—CH₂—OCH₃ | 389.1, 2.65 |
| 11 | 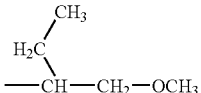 —CH(CH₂CH₃)—CH₂—OCH₃ | 476.2, 3.50 |
| 12 | —(CH₂)₂OCH₃ | 375.2, 2.48 |
| 13 | 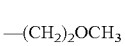 cyclopropyl | 357.1, 2.64 |
| 14 |  cyclobutyl | 371.1, 2.89 |
| 15 |  cyclopentyl | 385.2, 3.00 |
| 16 |  cyclohexyl | 399.1, 3.24 |
| 17 | 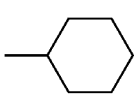 —CH(CH₃)—Ph | 421.2, 3.31 |
| 18 | 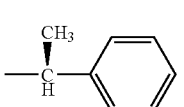 —CH₂-(2-F-C₆H₄) | 425.1, 3.29 |
| 19 |  —CH₂-(3-F-C₆H₄) | 425.1, 3.32 |
| 20 | 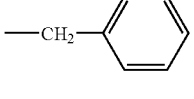 —CH₂-(4-F-C₆H₄) | 425.1, 3.31 |
| 21 | 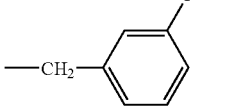 —CH₂-(2-Cl-C₆H₄) | 441.1, 3.49 |
| 22 | 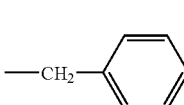 —CH₂-(3-Cl-C₆H₄) | 441.1, 3.57 |
| 23 | 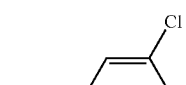 —CH₂-(4-Cl-C₆H₄) | 441.1, 3.57 |
| 24 | 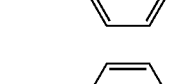 —CH₂-(2-OCH₃-C₆H₄) | 437.2, 3.27 |
| 25 | 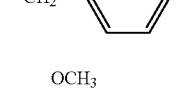 —CH₂-(3-OCH₃-C₆H₄) | 437.2, 3.27 |
| 26 | 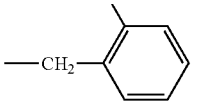 —CH₂-(4-OCH₃-C₆H₄) | 437.2, 3.22 |
| 27 | 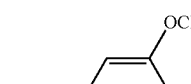 —CH₂-(2-pyridyl) | 408.0, 2.80 |
| 28 | 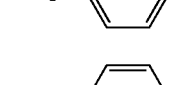 —CH₂-(3-pyridyl) | 408.0, 2.08 |
| 29 | 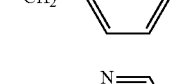 —CH₂-(4-pyridyl) | 408.0, 2.06 |
| 30 | 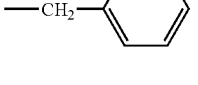 tolyl | 393.2, 3.44 |
| 31 | 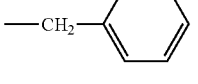 3-F-tolyl | 411.0, 3.61 |
| 32 | 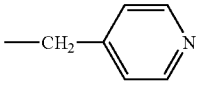 4-F-tolyl | 411.2, 3.52 |
| 33 | 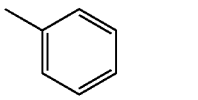 2-Cl-tolyl | 427.0, 3.52 |

TABLE 1-continued

| Example No. | R⁴ | Data MS/HPLC |
|---|---|---|
| 34 | 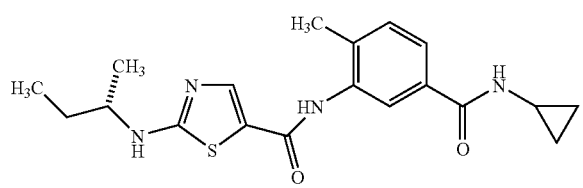 —CH₂- (3-fluoropyridin-2-yl) | 426.1, 2.83 |
| 35 | 3-methylpyrrolidine | 386.1, 1.98 |
| 36 | —(CH₂)₂OH | 361.1, 2.23 |
| 37 | —CH₂- (4-fluoropyridin-3-yl) | 426.1, 2.83 |

Example 38

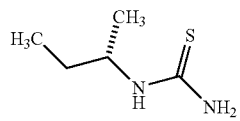

38A.

(38A)

To a solution of S-sec-butyl-amine (7.31 g, 0.1 mol) in chloroform (80 mL) at 0° C. was slowly added benzoyl isothiocyanate (13.44 mL, 0.1 mol). The mixture was allowed to warm to 10° C. and stirred for 10 min. The solvent was then removed under reduced pressure, and the residue was dissolved in MeOH (80 mL). An aqueous solution (10 mL) of a NaOH (4 g, 0.1 mol) was added to this solution, and the mixture was stirred at 60° C. another 2 h. The MeOH was then removed under reduced pressure, and the residue was stirred in water (50 mL). The precipitate was collected by vacuum filtration and dried to provide S-1-sec-butyl-thiourea (38A) (12.2 g, 92% yield). mp 133–134° C.; ¹H NMR (500 MHz, DMSO-D₆) δ 7.40 (s, 1H), 7.20 (br s, 1H), 6.76 (s, 1H), 4.04 (s, 1H), 1.41 (m, 2H), 1.03 (d, J=6.1 Hz, 3H), 0.81 (d, J=7.7 Hz, 3H); ¹³C NMR (125 MHz, DMSO-D₆) δ 182.5, 50.8, 28.8, 19.9, 10.3; LRMS m/z 133.2 (M+H); Anal. Calcd for C₅H₁₂N₂S: C, 45.41; H, 9.14.; N, 21.18; S, 24.25. Found: C, 45.49; H, 8.88; N, 21.32; S, 24.27.

38B.

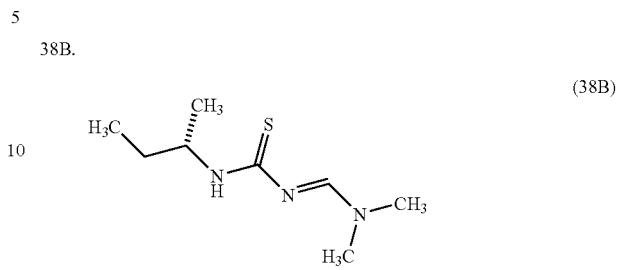

(38B)

To a solution of 38A (13.2 g, 0.1 mol) in EtOH (200 mL) was added DMF-DMA (16 mL, 0.12 mol). The solution was heated at 73° C. for 20 min. The solvent was removed under reduced pressure and the residue was dissolved in EtOAc (200 mL). The insoluble impurity was discarded by vacuum filtration. The filtrate was concentrated under reduced pressure and the residue was crystallized in hexane to provide S-1-sec-butyl-3-dimethylaminomethylene-thiourea (38B) (18.3 g, 98% yield). mp 69–70° C.; ¹H NMR (500 MHz, CDCl₃), ~3:2 mixture of isomers: major isomer δ 8.85 (s, 1H), 6.56 (br s, 1H), 4.48 (m, 1H), 3.10 (s, 3H), 3.00 (s, 3H), 1.49 (m, 2H); 1.19 (d, J=6.6 Hz, 3H), 0.92 (t, J=7.7 Hz, 3H); minor isomer δ 8.81 (s, 1H), 6.56 (br s, 1H), 4.22 (m, 1H), 3.13 (s, 3H), 3.06 (s, 3H), 1.60 (m, 2H); 1.12 (d, J=6.6 Hz, 3H), 0.87 (t, J=7.7 Hz, 3H); ¹³C NMR (100 MHz, CDCl₃) δ (191.9, 191.7), (164.0, 163.0), (52.1, 51.1), 41.7, (36.1, 35.9), (30.1, 29.6), (20.5, 19.9), (10.9, 10.8); LRMS m/z 188.33 (M+H); Anal. Calcd for C₈H₁₇N₃S: C, 51.29; H, 9.14.; N, 22.43; S, 17.12.
Found: C, 51.15; H, 9.21; N, 22.49; S, 17.14.

38C.

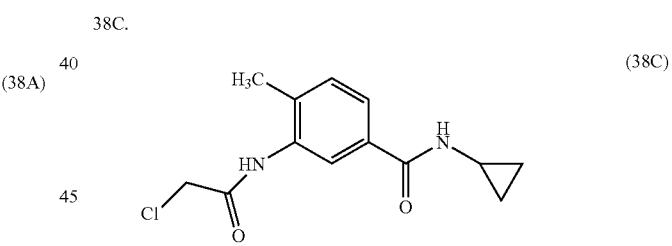

(38C)

To a suspension of 3-amino-N-cyclopropyl-4-methyl-benzamide hydrochloride (Compound 1D, 22.7 g, 0.1 mol) in acetone (200 mL) was added 4-methyl morpholine (42.4 mL, 0.3 mol). The solution was cooled to −20° C. and chloroacetyl chloride (12 mL, 0.15 mol) was added dropwise. The reaction mixture was stirred at −10° C. for 10 min before being quenched with H₂O (200 mL). The precipitate formed was collected by vacuum filtration and dried to provide 3-(2-chloro-acetylamino)-N-cyclopropyl-4-methyl-benzamide (38C) (25.3 g, 95% yield). mp: decomp 150° C.; ¹H NMR(500 MHz, DMSO-D₆) δ 9.83 (s, 1H), 8.39 (d, J=3.8 Hz, 1H), 7.82 (s, 1H), 7.58 (d, J=6.6 Hz, 1H), 7.28 (d, J=8.3 Hz, 1H), 4.32 (s, 2H), 2.82 (m, 1H), 2.22 (s, 3H), 0.66 (m, 2H), 0.56 (m, 2H); ¹³C NMR (100 MHz, DMSO-D₆) δ: 167.2, 165.4, 136.0, 135.8, 132.8, 130.5, 124.8, 124.7, 43.4, 23.4, 18.1, 6.0;
Anal. Calcd for C₁₃H₁₅ClN₂O₂: C, 58.54; H, 5.66; N, 10.50; Cl, 13.29. Found: C, 53.72; H, 5.95; N, 9.65; Cl, 13.52.

38D. Example 38

A solution of compound 38B (18.7 g, 0.1 mol) and 38C (26.7 g, 0.1 mol) in MeOH (100 mL) was stirred and refluxed for 6 h, then quenched with water. The precipitate was purified by crystallization from EtOH (active carbon), and the solid was stirred in water at 95° C. for 4 h. The final pure compound was collected by vacuum filtration and dried to provide Example 38. $^1$H NMR (500 MHz, DMSO) δ: 0.55 (m, 2H) 0.66 (td, J=7.01, 4.67 Hz, 2H) 0.87 (t, J=7.42 Hz, 3H) 1.14 (d, J=6.60 Hz, 3H) 1.51 (m, 2H) 2.22 (s, 3H) 2.83 (m, 1H) 3.62 (m, J=13.33, 6.87, 6.74 Hz, 1H) 7.30 (d, J=8.25 Hz, 1H) 7.60 (dd, J=8.25, 1.65 Hz, 1H) 7.73 (d, J=1.10 Hz, 1H) 7.89 (s, 1H) 8.10 (d, J=7.70 Hz, 1H) 8.37 (d, J=3.85 Hz, 1H) 9.61 (s, 1H); $^{13}$C NMR (500 MHz, DMSO) δ: 5.65, 10.32, 17.88, 19.70, 23.02, 28.60, 51.96, 120.07, 124.47, 125.55, 130.06, 132.30, 136.06, 137.11, 143.06, 159.72, 166.82, 171.21; m/z 373.20 [M+H]; Anal. Calcd for $C_{19}H_{24}N_4O_2S \cdot H_2O$: C, 58.44; H, 6.71; N, 14.35; S, 8.210. Found: C, 58.44; H, 6.47; N, 14.37; S, 8.18.

Alternate Methods to Produce Example 38

38E.

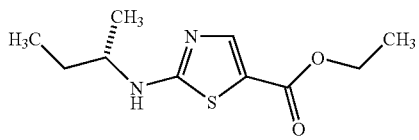
(38E)

38E.1.

A solution of ethyl β-ethoxyacrylate (14.2 mL, 98 mmol) in dioxane (40 mL) and water (40 mL) was cooled to −8° C., NBS (19.2 g, 108 mmol) was added, and the reaction mixture was allowed to warm to room temp. The solution was stirred at room temp for 1 h, S-1-sec-butyl-thiourea (Compound 38A, 13 g, 98 mmol) was added, and the reaction was heated to 80° C. for 5 h. The solution was cooled with ice, and NH$_4$OH (45 mL) was added, then the organic layers were extracted with ethyl acetate (500 mL, then 2×50 mL). The combined organic layers were washed with brine, dried over Na$_2$SO$_4$, filtered and concentrated in vacuo to a thick oil which was used without further purification.

38E.2.

Alternatively to Step 38E.1, compound 38E was prepared by heating a solution of compound 38B (509 mg, 2.7 mmol) and ethyl bromoacetate (0.32 mL, 2.7 mmol) in EtOH (10 mL), for 30 minutes at 75° C. The solution was cooled, concentrated to a thick oil and used directly in the next step.

38F.

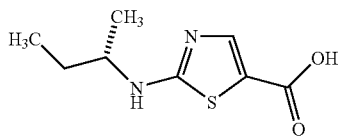
(38F)

To a solution of compound 38E (2.7 mmol) in THF (3 mL) and MeOH (3 mL) was added 1N NaOH (8 mL) and the reaction was heated at 60° C. for 18 h. The reaction mixture was cooled, concentrated in vacuo, and acidified with 1N HCl to pH 4–5. The solids were stirred for 1 h, filtered and rinsed with water (2×) to give, after drying, compound 38F (463 mg, 85% $^1$H NMR (400 MHz, DMSO-D6) δ 12.43 (s, 1H), 8.25 (d, J=7.8 Hz, 1H), 7.65 (s, 1H), 3.62 (m, 1H), 1.51 (m, 2H), 1.14 (d, J=6.5 Hz, 3H), 0.87 (t, J=7.4 Hz, 3H); $^{13}$C NMR (125 MHz, DMSO-D6) δ 172.5, 163.1, 147.7, 115.4, 52.3, 28.8, 19.9, 10.6; LRMS m/z 201.1 (M+H).

38G. Example 38

A solution of compound 38F was reacted with 3-amino-N-cyclopropyl-4-methylbenzamide hydrochloride, to produce Example 38, following the method described below in Step 129D, using EDC, HOBt, and DMF.

Example 39

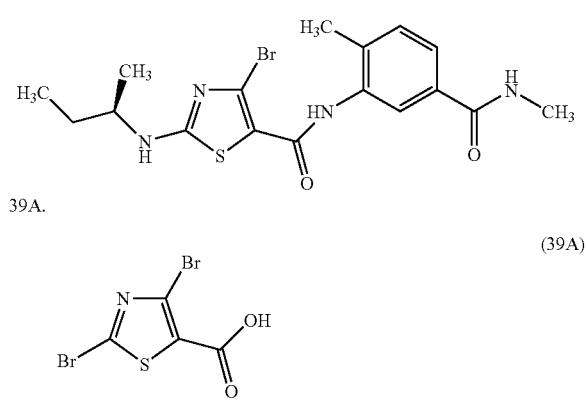

39A.
(39A)

To a solution of LDA (4.35 mmol) in THF (30 mL) at −78° C. was added a solution of 2,4-dibromothiazole (1.0 g, 3.95 mmol) in THF (20 mL) via canula over 5 min. Dry CO$_2$ gas was passed through the reaction vessel, and the reaction mixture was allowed to warm to −60° C. The reaction was stirred at this temperature while the CO$_2$ sweep was maintained for 40 min. The reaction was then allowed to slowly warm to rt and was stirred for 2 h. The reaction was quenched with 10% HCl, diluted with water and extracted with EtOAc. The organic extracts were concentrated to give the crude product, compound 39A (0.85 g, 75% yield).

39B.

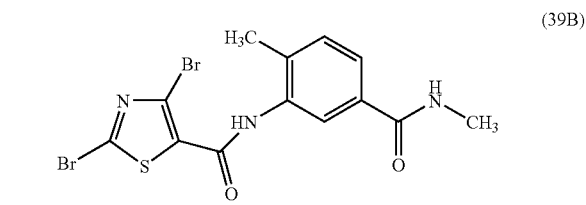
(39B)

To a 15 mL RBF was added acid 39A (131 mg, 0.46 mmol), 2-methyl-5-methylcarboxamido-aniline (114 mg, 0.57 mmol), HATU (223 mg, 0.57 mmol) and NMP (1 mL) followed by DIPEA (99 μL, 0.57 mmol), and the reaction vessel was heated to 50° C. for 5 h. An additional amount of HATU (55 mg) was added and heating continued for 2 h at 55–60° C. Water (1 mL) was added, and the reaction mixture was cooled to rt. Aqueous NaHCO$_3$ was added to make the solution basic followed by dilution with water (5 mL). The resulting solids were filtered and washed with water to give, after drying, compound 39B (161 mg, 82% yield) as a white solid. $^1$H NMR: (DMSO-D$_6$, 400 MHz) δ 10.17 (s, 1H), 8.48 (m, 1H), 8.00 (s, 1H), 7.72 (d, J=7.9 Hz, 1H), 7.43 (d, J=7.9 Hz, 1H), 2.84 (d, J=4.5 Hz, 3H), 2.38 (s, 3H); HPLC rt 3.30 min, 98.9% purity (Condition A).

39C. Example 39

Example 39 was prepared from compound 39B following the general method described above for Example 1 (Scheme 1), Step 1F. LCMS 459.1/460.1 (M+MeOH); HPLC rt 3.72 min, 99.5% purity (Condition A).

Example 40

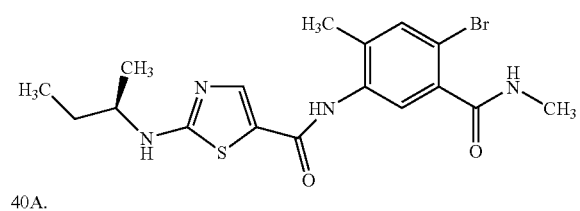

40A.

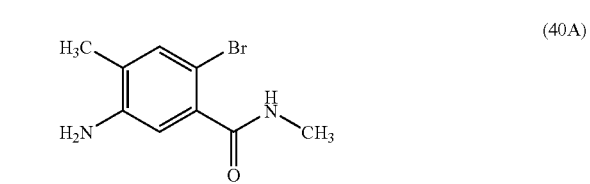

(40A)

To a solution of 2-methyl-5-methylcarboxamido-aniline (165 mg, 1 mmol) in DMF (5 mL) at 0° C. was added NBS (180 mg, 1 mmol). The solution was stirred for 10 minutes and slowly water (20 mL) was added. The product was extracted with EtOAc (3×30 mL), dried over Na$_2$SO$_4$, filtered and concentrated to an oil. The residue was purified on silica gel (50% EtOAc/heptane to 75% EtOAc/heptane and finally 100% EtOAc) to give 270 mg of compound 40A. $^1$H NMR: (CDCl$_3$, 400 MHz) δ 7.22 (s, 1H), 6.95 (s, 1H), 6.11 (br s, 1H), 3.00 (d, J=5.0 Hz, 3H), 2.14 (s, 3H); HPLC rt 1.05 min, 99.9% purity (Condition A).

40B.

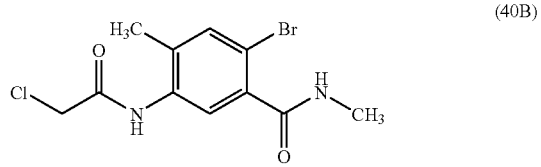

(40B)

To a solution of compound 40A (94 mg, 0.38 mmol) in acetone (4 mL) at 0° C. was added DIPEA (68 µL, 0.39 mmol) followed by 2-chloroacetylchloride (31 µL, 0.39 mmol). The solution was stirred for 60 min. and another aliquot of 2-chloroacetylchloride (4 µL) was added. Water was added (94 mL), and the acetone removed in vacuo. The solids were stirred rapidly for 1 h, filtered and washed with water to give compound 40B (104 mg, 84% yield). $^1$H NMR: (CDCl$_3$, 400 MHz) δ 8.28 (s, 1H), 8.03 (s, 1H), 7.44 (s, 1H), 6.01 (br s, 1H), 4.23 (s, 2H), 3.01 (d, J=5.0 Hz, 3H), 2.17 (s, 3H); LCMS 320.99 (M+H); HPLC rt 2.38 min, 98.8% purity (Condition A).

40C. Example 40

The compound of Example 40 was prepared using compound 40B and the methods outlined for Example 38. (87 mg, 83% yield). $^1$H NMR: (DMSO-D$_6$, 400 MHz) δ 9.56 (s, 1H), 8.29 (m, 1H), 8.15 (d, J=7.9 Hz, 1H), 7.90 (s, 1H), 7.54 (s, 1H), 7.33 (s, 1H), 3.64 (m, 1H), 2.73 (d, J=4.6 Hz, 3H), 2.23 (s, 3H), 1.55)m, 1H), 1.15 (d, J=6.5 Hz, 3H), 0.89 (t, J=7.4 Hz, 3H); LCMS 427.1 (M+2H); HPLC rt 3.14 min, 99.8% purity (Condition A).

Example 41

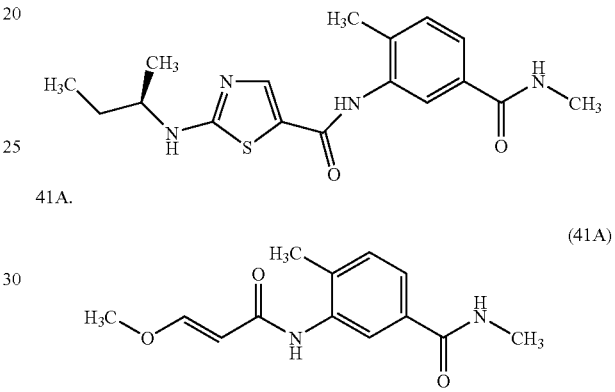

To a solution of 3-amino-N-methyl-4-methylbenzamide hydrochloride (1.0 g, 5 mmol) in acetone (10 mL) at 0° C. was added pyridine (1.2 mL, 15 mmol) dropwise via syringe. 3-Methoxyacryloyl chloride (0.72 mL. 6.5 mmol) was added and the reaction stirred at room temperature for 1 h. The solution was cooled again to 0° C. and 1N HCl (1.5 mL) was added dropwise via pipet. The reaction mixture was stirred for 5 min, then water (8.5 mL) was added via an addition funnel. The acetone was removed in vacuo and the resulting solution stirred for 4 h. Crystallization began within 15 min. After stirring for 4 h, the vessel was cooled in an ice bath for 30 min, filtered, and rinsed with ice cold water (2×3 mL) to give compound 41A (0.99 g, 78% yield) as a white solid. $^1$H NMR (400 MHz, CDCl$_3$) δ 8.95 (s, 1H), 8.12 (br s, 1H), 7.76 (s, 1H), 7.29 (m, 2H), 7.05 (d, J=7.9 Hz, 1H), 5.47 (d, J=12.3 Hz, 1H), 3.48 (s, 3H), 2.54 (d, J=4.7 Hz, 3H), 2.03 (s, 3H); HPLC rt 2.28 min (Condition A).

41B. Example 41

To a 50 mL RBF containing the above compound 41A (0.5 g, 2.0 mmol) was added THF (2.5 mL) and water (2 mL), followed by NBS (0.40 g, 2.22 mmol), and the solution was stirred for 90 min. R-sec-butylthiourea (267 mg, prepared as described above in Example 38 for S-1-sec-butyl-thiourea [38A]), was added, and the solution was heated to 75° C. for 8 h. Conc. NH$_4$OH was added to adjust the pH to 10 followed by the addition of EtOH (15 mL). Water (15 mL) was added and the slurry stirred for 16 h, filtered, and washed with water to give Example 41 as a light brown solid (0.48 g, 69% yield, 98% purity). MS 347.1; HPLC 2.59.

Examples 42–66

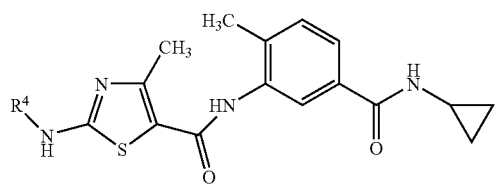

Compounds having the formula (Id) wherein $R^4$ has the values set forth in Table 2, were prepared following the same or similar method described for Example 1, except in Step 1A, ethyl 2-amino-4-methyl thiazole-5-carboxylate was used in place of methyl 2-amino-5-thiazolyl carboxylate.

TABLE 2

| Example No. | $R^4$ | Data MS/HPLC |
|---|---|---|
| 42 | —CH$_2$—CH$_3$ | 359.2, 2.34 |
| 43 | —(CH$_2$)$_2$CH$_3$ | 373.3, 2.56 |
| 44 | —CH—(CH$_3$)$_2$ | 373.2, 2.49 |
| 45 | —CH(CH$_3$)—CH$_2$—CH$_3$ | 387.2, 2.74 |
| 46 | —CH$_2$—CH(CH$_3$)$_2$ | 387.2, 2.83 |
| 47 | —(CH$_2$)$_2$OCH$_3$ | 389.2, 2.39 |
| 48 | cyclopropyl | 371.2, 2.50 |
| 49 | cyclobutylmethyl | 385.2, 2.74 |
| 50 | cyclopentylmethyl | 399.2, 2.84 |
| 51 | cyclohexylmethyl | 413.1, 3.08 |
| 52 | —CH$_2$-phenyl | 421.1, 3.13 |
| 53 | —CH(CH$_3$)-phenyl | 435.2, 3.22 |
| 54 | —CH$_2$-(2-F-phenyl) | 439.2, 3.21 |
| 55 | —CH$_2$-(3-F-phenyl) | 439.1, 3.28 |
| 56 | —CH$_2$-(4-F-phenyl) | 439.1, 3.23 |
| 57 | —CH$_2$-(2-Cl-phenyl) | 455.2, 3.46 |
| 58 | —CH$_2$-(3-Cl-phenyl) | 455.1, 3.52 |
| 59 | —CH$_2$-(4-Cl-phenyl) | 455.1, 3.51 |
| 60 | —CH$_2$-(2-OCH$_3$-phenyl) | 451.2, 3.14 |
| 61 | —CH$_2$-(3-OCH$_3$-phenyl) | 451.1, 3.18 |
| 62 | —CH$_2$-(4-OCH$_3$-phenyl) | 451.1, 3.12 |
| 63 | —CH$_2$-(2-pyridyl) | 422.1, 2.32 |
| 64 | —CH$_2$-(3-pyridyl) | 422.1, 2.17 |
| 65 | —CH$_2$-(4-pyridyl) | 422.0, 2.16 |
| 66 | 4-F-2-methylphenyl | 425.1, 3.58 |

Example 67

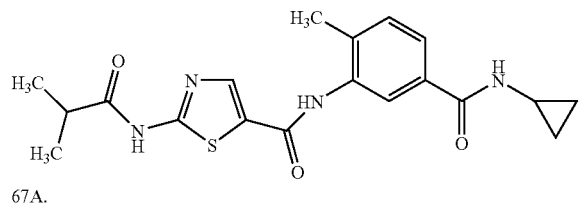

67A.

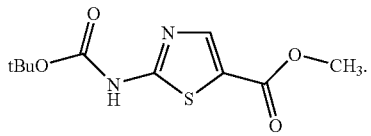

To a solution of methyl 2-amino-5-thiazoyl carboxylate (1.0 g, 6.4 mmol) in THF (20 mL) was added di-t-butyl-dicarbonate (1.6 g, 7.1 mmol), and the solution was heated at reflux for a total of 16 h. The reaction mixture was poured into EtOAc (100 mL) and washed with water (25 mL), NaHCO$_3$ (sat. aq., 25 mL), 1N HCl (25 mL), and the brine (25 mL). The organic layer was dried over Na$_2$SO$_4$, filtered and concentrated to give the N-Boc protected thiazole 67A (1.6 g, 95% yield). $^1$H NMR: (CDCl$_3$, 400 MHz) δ 12.45 (s, 1H), 8.04 (s, 1H), 3.88 (s, 3H), 1.61 (s, 9H); LCMS 259.0 (M+H); HPLC rt 3.46 min.

67B.

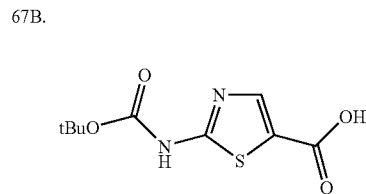

To a solution of compound 67A (1.6 g, 6.1 mmol) in THF (15 mL) was added 1N NaOH (15 mL), and the reaction was stirred at RT overnight. An additional 6 mL aliquot of 1N NaOH was added after 18 h and then the reaction vessel was heated to 55° C. for 1 h. The reaction was cooled in an ice bath and neutralized with 1N HCl (18 mL) and the slurry stirred for 1 h. The solids were filtered and rinsed with cold water (2×5 mL) to give acid 67B as a white solid (1.2 g, 84% yield). $^1$H NMR: (DMSO-D$_6$, 400 MHz) δ 12.98 (s, 1H), 11.95, (s, 1H), 7.96 (s, 1H), 1.50 (s, 9H); LCMS 245.0 (M+H); HPLC rt 3.04 min.

67C.

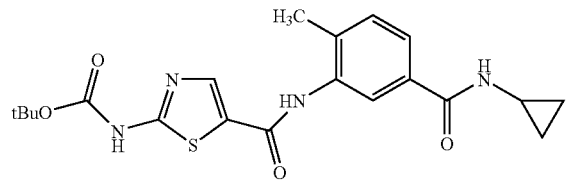

In a 25 mL RBF was added compound 67B (160 mg, 0.65 mmol), HOBt (105 mg, 0.78 mmol), EDCI (150 mg, 0.78 mmol), compound 1D (177 mg, 0.78 mmol) and NMP (3 mL), and the mixture was stirred at RT for 1 h. DIPEA was added (0.14 mL, 0.78 mmol), and the reaction vessel was heated to 80° C. for 5 h, cooled to RT, and water was added (12 mL) dropwise. The solids were filtered and rinsed with cold water (2×5 mL) to give compound 67C as a tan solid (230 mg, 83% yield). $^1$H NMR: (MeOD$_4$, 400 MHz) δ 7.89 (s, 1H), 7.54 (d, J=1.7 Hz, 1H), 7.44 (d, J=1.8. 8.0 Hz, 1H), 7.17 (d, J=8.0 Hz, 1H), 2.64 (m, 1H), 2.14 (s, 3H), 1.37 (s, 9H), 0.60 (m, 2H), 0.43 (m, 2H); LCMS 417.0 (M+H); HPLC rt 3.47 min.

67D.

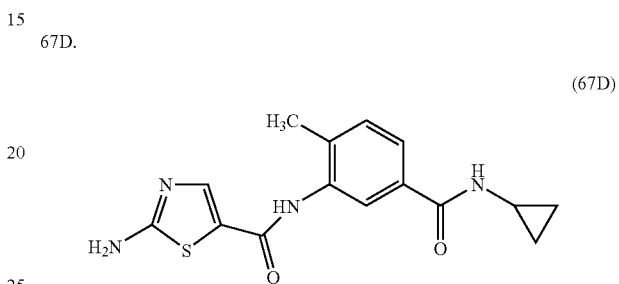

Compound 67C (1.6 g, 3.8 mmol) was added to 4N HCl in dioxane (10 mL). The reaction was stirred for 7 h and concentrated to an oil. EtOH (25 mL) was added and the solids were stirred for 30 minutes at room temperature, then cooled to −40° C. for 2 h. The solids were filtered and washed with cold EtOH to give compound 67D (1.1 g, 84%) as the HCl salt. $^1$H NMR: (DMSO-D$_6$, 400 MHz) δ 9.88 (br s, 1H), 8.50 (br s, 1H), 8.40 (d, J=4.1 Hz, 1H), 8.00 (s, 1H), 7.74 (s, 1H), 7.63 (d, J=8.1 Hz, 1H), 7.32 (d, J=8.0 Hz, 1H), 2.83 (m, 1H), 2.24 (s, 3H), 0.68 (m, 2H), 0.56 (m, 2H); LCMS 317.0 (M+H); HPLC rt 1.90 min.

Alternatively, compound 67D was prepared by adding concentrated NH$_4$OH to compound 1E (100 mg) in EtOH (0.25 mL), and heating the mixture to 150° C. for 1 h. The reaction mixture was concentrated to remove the EtOH and the precipitated solids filtered and washed with water to give amine 67D as an off-white solid (62 mg, 75% yield).

67E. Example 67

Isobutyryl chloride (35 μL, 0.033 mmol) was added to a suspension of compound 67D (10 mg, 0.032 mmol) in CH$_2$Cl$_2$ (1 mL) at 0° C. TEA (4.5 μL, 0.033 mmol) was added and the mixture stirred for 2h at 0° C. The solvent was removed with a rotary evaporator, and to the residue was added EtOH (50 μL), water (1 mL) and NaHCO$_3$ (100 μL, sat. aq). The solid was filtered, washed with water and dried to give Example 67 (6 mg, 49% yield). LCMS 387.7 (M+H); HPLC rt 3.10 min.

Example 68

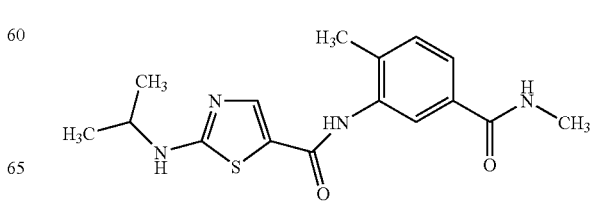

68A.

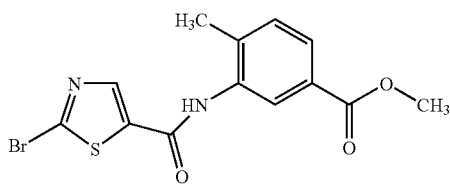
(68A)

Compound 68A was prepared according to the procedure described in Example 1, Step 1E, using compound 1C and methyl 3-amino-4-methyl benzoate, HPLC rt 3.29 min.

68B.

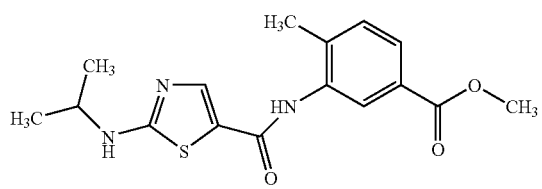
(68B)

Compound 68B was prepared from 68A according to the procedure described for Example 1, Step 1F. LCMS 334.1 (M+H); HPLC rt 2.89 min.

68C.

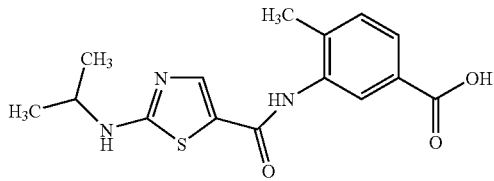

To a solution of compound 68B in MeOH (1 mL) was added 10% NaOH (0.3 mL), and the reaction mixture was heated at 50° C. for 18 h. The reaction was cooled to RT and neutralized with 1N HCl. The mixture was stirred, filtered, and rinsed with water to give the above compound 68C (56 mg, 59% yield) as a solid. LCMS 320.1 (M+H); HPLC rt 2.57 min.

68D. Example 68

Example 68 was prepared from compound 61C by reaction with methylamine as outlined in Scheme 7. LCMS 320.1 (M+H); HPLC rt=2.29.

Examples 69–90

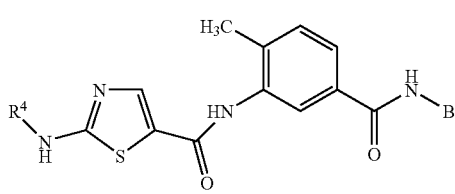
(Ie)

Compounds having the above formula, wherein $R^4$ and B have the values set forth in Table 3 were prepared using methods analogous to those described above for Examples 1, 67 and 68. In some instances, intermediates 69A and 69B below, prepared following the same method described above for compound 68C, were used to prepare compounds reported in Table 3.

TABLE 3

MS/HPLC: 334.1, 2.99
(Compound 69A)

MS/HPLC: 334.1, 3.00
(Compound 69B)

| Example No. | $R^4$ | B | Data MS/HPLC |
|---|---|---|---|
| 69 | —(CH$_2$)$_2$CH$_3$ | H | 319.2, 2.40 |
| 70 | —CH—(CH$_3$)$_2$ | H | 319.1, 2.14 |
| 71 | —CH(CH$_3$)—CH$_2$—CH$_3$ | H | 333.1, 2.43 |
| 72 | —CH(CH$_3$)—CH$_2$—CH$_3$ | H | 333.1, 2.48 |
| 73 | cyclopentyl | H | 345.1, 2.61 |
| 74 | —(CH$_2$)$_2$CH$_3$ | —CH$_2$—CH$_3$ | 347.2, 2.63 |
| 75 | —CH—(CH$_3$)$_2$ | —CH$_2$—CH$_3$ | 347.2, 2.53 |
| 76 | —CH(CH$_3$)—CH$_2$—CH$_3$ | —CH$_2$—CH$_3$ | 361.2, 2.78 |
| 77 | —CH(CH$_3$)—CH$_2$—CH$_3$ | —CH$_2$—CH$_3$ | 361.2, 2.78 |
| 78 | —(CH$_2$)$_2$OCH$_3$ | —CH$_2$—CH$_3$ | 363.1, 2.36 |
| 79 | cyclopentyl | —CH$_2$—CH$_3$ | 373.2, 2.91 |
| 80 | —(CH$_2$)$_2$CH$_3$ | CH$_3$ | 333.1, 2.41 |
| 81 | —CH—(CH$_3$)$_2$ | CH$_3$ | 333.1, 2.39 |
| 82 | —CH(CH$_3$)—CH$_2$—CH$_3$ | CH$_3$ | 347.2, 2.58 |
| 83 | —(CH$_2$)$_2$OCH$_3$ | CH$_3$ | 349.1, 2.15 |

TABLE 3-continued

MS/HPLC: 334.1, 2.99
(Compound 69A)

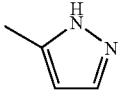

MS/HPLC: 334.1, 3.00
(Compound 69B)

| Example No. | R$^4$ | B | Data MS/HPLC |
|---|---|---|---|
| 84 | 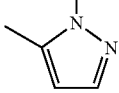 | CH$_3$ | 359.1, 2.69 |
| 85 | —CH—(CH$_3$)$_2$ | 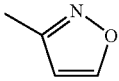 | 385.2, 2.57 |
| 86 | —CH—(CH$_3$)$_2$ |  | 399.2, 2.17 |
| 87 | —CH—(CH$_3$)$_2$ |  | 386.1, 2.76 |
| 88 | H | CH$_3$ | 291.2, 1.69 |
| 89 | —CH—(CH$_3$)$_2$ | CH$_3$ | 347.1, 2.78 |
| 90 | —CH—(CH$_3$)$_2$ | —CH$_2$—CH$_3$ | 361.2, 3.00 |

Examples 91–101

 (If)

Compounds having the above formula (If), wherein R$^4$ and B have the values set forth in Table 4, were prepared using methods analogous to those described above for Examples 1, 67 and 68 using an appropriate alkyl isocyanate or acid chloride in THF/pyr (2/1) at reflux.

TABLE 4

| Example No. | R$^4$ | B | Data MS/HPLC |
|---|---|---|---|
| 91 | —CH$_2$—CH$_3$ | 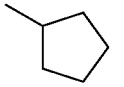 | 373.2, 2.91 |
| 92 | —CH—(CH$_3$)$_2$ |  | 387.7, 3.10 |
| 93 | —(CH$_2$)$_2$CH$_3$ | 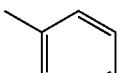 | 387.2, 3.14 |
| 94 |  |  | 413.6, 3.41 |
| 95 |  |  | 421.5, 3.40 |
| 96 | —NH—CH$_2$—CH$_3$ | 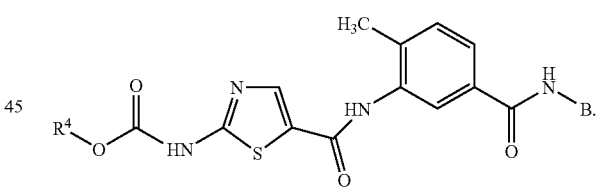 | 388.2, 2.86 |
| 97 | —NH—CH—(CH$_3$)$_2$ |  | 402.1, 3.10 |
| 98 | —NH—(CH$_2$)$_2$—CH$_3$ |  | 402.0, 3.14 |
| 99 | —CH—(CH$_3$)$_2$ | H | 347.1, 2.82 |
| 100 | —CH—(CH$_3$)$_2$ | CH$_3$ | 361.2, 2.89 |
| 101 | —CH—(CH$_3$)$_2$ | —CH$_2$—CH$_3$ | 375.1, 3.08 |

Examples 102–106

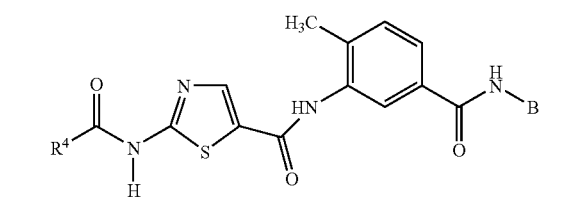 (Ig)

Compounds having the above formula (Ig), wherein R$^4$ and B have the values set forth in Table 5, were prepared using methods analogous to those described above for Examples 1, 67 and 68.

TABLE 5

| Example No. | R$^4$ | B | Data MS/HPLC |
|---|---|---|---|
| 102 | —CH$_2$—CH$_3$ | CH$_3$ | 361.0 (M − H), 2.87 |
| 103 | —CH$_2$—CH$_3$ | —CH$_2$—CH$_3$ | 375.0 (M − H), 3.03 |
| 104 | —CH$_2$—CH$_3$ | 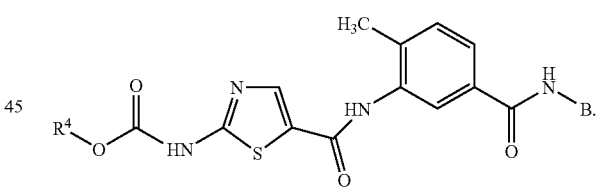 | 387.1 (M − H), 3.08 |
| 105 | —CH$_3$ | 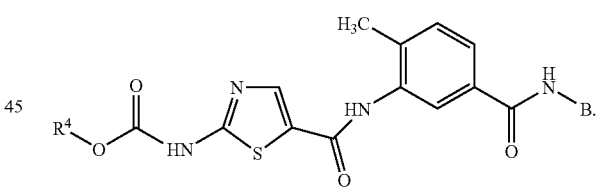 | 375.0, 2.83 |

TABLE 5-continued

| Example No. | R⁴ | B | Data MS/HPLC |
|---|---|---|---|
| 106 | —CH—(CH₃)₂ | cyclopropyl | 401.0, 3.28 |

Example 107

NaH (0.9 mmol) was dissolved in iso-propanol at 0° C. Compound 1E (18 mg, 0.047 mmol) was added and the solution heated at 120° C. for 30 min. The mixture was concentrated, water was added (0.5 mL), and the mixture was stirred rapidly for 18 h, then filtered and rinsed with more water. The solid was dried to give Example 107 (15 mg, 88% yield) as a white solid. MS⁺=360.1, HPLC ret. t=3.36.

Examples 108–112

Compounds having the formula (Ih), wherein $R^3$ and $R^4$ have the values listed in Table 6 were prepared following the methods described for Example 107 and in Scheme 1.

TABLE 6

| Example No. | R⁴ | R³ | Data MS/HPLC |
|---|---|---|---|
| 108 | —CH₃ | H | 332.2, 2.87 |
| 109 | —CH₂—CH₃ | H | 345.1, 3.17 |
| 110 | —(CH₂)₂CH₃ | H | 360.2, 2.83 |
| 111 | cyclopentyl | H | 386.2, 3.41 |
| 112 | —CH₂—CH₃ | CH₃ | 360.1, 3.24 |

Examples 113–124

Compounds having the above formula (Ii), wherein $R^3$, $R^4$ and $R^5$ have the values listed in Table 7, were prepared following the methods set forth above in Examples 1, 67 and 68.

TABLE 7

| Example No. | R⁴ | R⁵ | R³ | Data MS/HPLC |
|---|---|---|---|---|
| 113 | CH₃ | CH₃ | H | 345.2, 2.54 |
| 114 | —CH₂—CH₃ | CH₃ | H | 359.2, 2.79 |
| 115 | R⁴ and R⁵ together with N combine to form pyrrolidine | | H | 371.2, 3.5 |
| 116 | R⁴ and R⁵ together with N combine to form piperidine | | H | 385.2, 3.21 |
| 117 | R⁴ and R⁵ together with N combine to form morpholine | | H | 387.1, 2.83 |
| 118 | R⁴ and R⁵ together with N combine to form N-methylpiperazine | | H | 400.3, 2.06 |
| 119 | CH₃ | CH₃ | CH₃ | 359.2, 2.31 |
| 120 | —CH₂—CH₃ | CH₃ | CH₃ | 373.2, 2.55 |
| 121 | R⁴ and R⁵ together with N combine to form pyrrolidine | | CH₃ | 385.2, 2.47 |

TABLE 7-continued

| Example No. | R⁴ | R⁵ | R³ | Data MS/HPLC |
|---|---|---|---|---|
| 122 | R⁴ and R⁵ together with N combine to form | | CH₃ | 399.2, 3.05 |
| 123 | R⁴ and R⁵ together with N combine to form | | CH₃ | 401.2, 2.87 |
| 124 | R⁴ and R⁵ together with N combine to form | | CH₃ | 414.2, 2.19 |

Examples 125–128

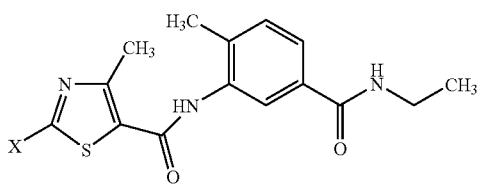
(Ij)

Compounds having the above formula (Ij), wherein X has the values listed in Table 8 were prepared following the methods set forth above in Examples 1, 67 and 68.

TABLE 8

| Example No. | X | Data MS/HPLC |
|---|---|---|
| 125 | | 347.1, 2.52 |
| 126 | | 361.3, 2.30 |
| 127 | | 359.1, 2.45 |
| 128 | | 348.4, 3.20 |

Example 129

129A.

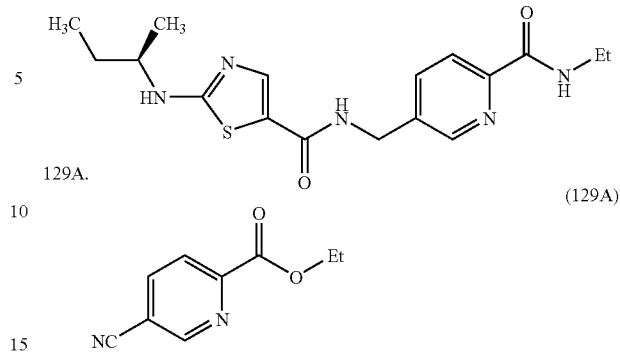
(129A)

To a Parr bomb was added 2-chloro-5-cyanopyridine (1.1 g, 7.9 mmol), DPPF (2.4 g), Pd(MeCN)₂Cl₂ (84 mg), EtOH (15 mL), and TEA (1.21 mL). The vessel was sealed, evacuated and charged to 50 psi with CO gas. The vessel was then heated to 130° C. for 18 h. The vessel was cooled and the CO gas was carefully vented. The mixture was filtered through celite, rinsed with EtOH, and concentrated. The product was purified via silica gel chromatography (20% EtOAc/hexane then 35% EtOAc/hexane) to afford compound 129A (0.923 g, 66% yield) as a white solid. H NMR (400 MHz, CDCl₃) δ 8.94 (d, J=1.9 Hz, 1H), 8.18 (dd, J=0.7, 8.1 Hz, 1H), 8.07 (dd, J=2.2, 8.1 Hz, 1H), 4.45 (q, J=7.1 Hz, 2H), 1.40 (t, J=7.1 Hz, 3H); LCMS 149.01 (M+H); HPLC rt 2.72 min, 99% purity (Condition A).

129B.

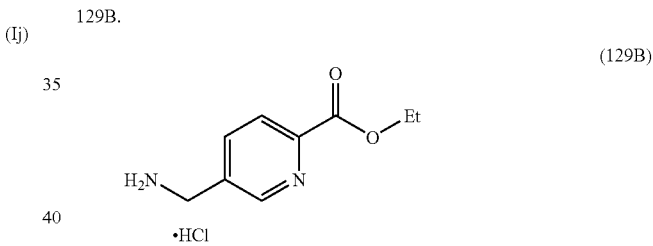
(129B)

Compound 129A (260 mg, 1.48 mmol) was converted to 129B using the procedure outlined below for converting compound 130A to 130B. The product was crystallized from EtOH/EtOAc (1/1) to give (300 mg, 81% yield) as a white solid. ¹H NMR (400 MHz, MeOD-4) δ 9.01 (d, J=1.4 Hz, 1H), 8.66 (dd, J=1.9, 8.2 Hz, 1H), 8.46 (d, J=8.2 Hz, 1H), 4.48 (q, J=7.1 Hz, 2H), 4.40 (s, 3H), 1.38 (t, J=7.2 Hz, 3H); LCMS 181.08 (M+H); HPLC rt 0.53 min, 92% purity (Condition B).

129C.

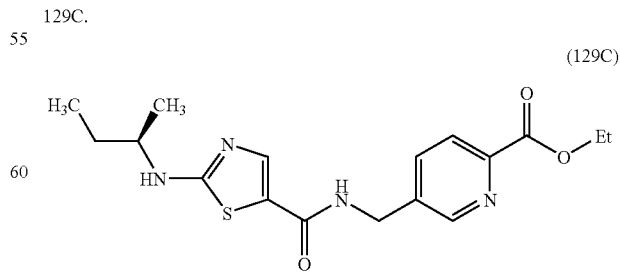
(129C)

To a solution of compound 133C (37 mg, 0.18 mmol) in CH₂Cl₂ (1 mL) was added DMF (2 μL) followed by SOCl₂

(37 μL, 0.28 mmol). The solution was stirred for 3 h and the solvent removed. The residual oil was dried under high vacuum for 1 h. To the crude acid chloride was then added CH$_2$Cl$_2$ (2 mL) and compound 129B (56 mg. 0.26 mmol) followed by DIPEA (0.13 mL) at 0° C. The reaction was stirred for 3 h and the solvent removed. Water (3 mL) was added and the solution made basic with aq NaHCO$_3$. The solids were stirred for 18 h, filtered, and rinsed with water (3×1 mL) to afford compound 129C (52 mg, 78% yield). LCMS 363.3 (M+H); HPLC rt 2.82 min, 92% purity (Condition A).

129D. Example 129

To a solution of compound 129C (467 mg, 0.13 mmol) in THF (0.25 mL) and MeOH (0.25 mL) was added 1N NaOH (0.25 mL). The solution was stirred for 30 min and then 1N HCl (0.25 mL) was added. The organic solvents were removed in vacuo and water (0.5 mL) was added. Stirring was continued for 1 h, then the solids were filtered and rinsed with water (2×0.5 mL) to afford the crude carboxylic acid (34 mg, 80% yield). To this acid (22.4 mg, 0.067 mmol) was added EDCI (15.4 mg, 0.08 mmol), HOBt (11 mg, 0.08 mmol) and 1/1 DMF/CH$_2$Cl$_2$ (0.4 mL). The solution was stirred for 15 min, then ethylamine hydrochloride (12.2 mg, 0.15 mmol) and DIPEA (26 μL, 0.15 mmol) were added. The reaction was stirred for 1 h, filtered to remove trace solids and concentrated in vacuo. Water (1 mL) was added dropwise with stirring and the resulting solids stirred rapidly for 1 h. The solids were filtered and washed with water to give Example 129 (20.2 mg, 83% yield). LCMS 362.2 (M+H); HPLC rt 2.60 min, 99% purity (Condition A).

Example 130

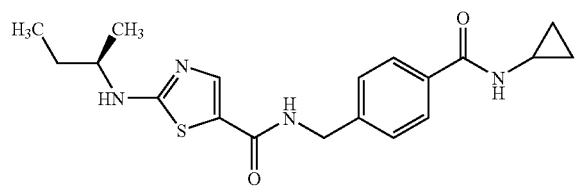

130A.

(130A)

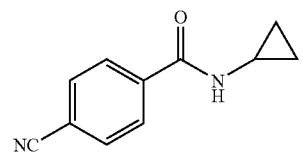

To a solution of p-cyanobenzoyl chloride (1.67 g, 10.8 mmol) in CH$_2$Cl$_2$ (40 mL) was added cyclopropylamine (1.5 mL, 22 mmol) in one portion. The reaction mixture was stirred for 1 h, then sat. aq. NaHCO$_3$ (10 mL) was added, and then the reaction was diluted with water (20 mL). The layers were separated and the organic layer was washed with brine (25 mL). The organic solution was dried over Na$_2$SO$_4$, filtered and concentrated to give compound 130A as an oil which was used without further purification (1.73 g, 86% yield). $^1$H NMR (400 MHz, CDCl$_3$) δ 7.76 (d, J=8.3 Hz, 2H), 7.65 (d, J=8.2 Hz, 2H), 6.24 (br s, 1H), 2.85 (m, 1H), 0.84 (m, 2H), 0.58 (m, 2H). HPLC rt 2.22 min, 95% purity (Condition A).

130B.

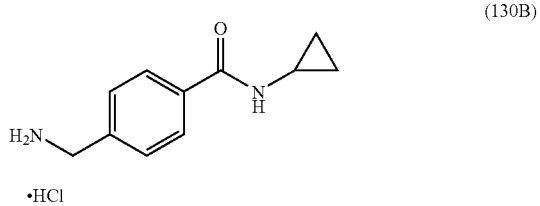

(130B)

To a solution of compound 130A (1.19 g, 6.4 mmol) in EtOH (80 mL) was added conc. HCl (5 mL) followed by 5% Pd—C (0.8 g, wet). The reaction vessel was evacuated and backfilled with hydrogen three times and then stirred for a total of 3 h. The solution was filtered through Celite, and the filter pad rinsed with MeOH. The solvents were removed in vacuo to afford a white solid. EtOH (25 mL) was added to the solid, the solution stirred for 2 h, cooled to 0° C. and filtered. The solids were rinsed with cold EtOH and dried on the filter overnight to afford compound 130B (1.19 g, 82% yield) as a white solid. $^1$H NMR (400 MHz, DMSO-D$_6$) δ 8.51 (d, J=3.7 Hz, 1H), 8.39 (br s, 2H), 7.85 (d, J=8.2 Hz, 2H), 7.54 (d, J=8.1 Hz, 2H), 4.59 (s, 2H), 2.85 (m, 1H), 0.70 (m, 2H), 0.57 (m, 2H). LCMS 191.09 (M+H).

130C.

Example 130 was prepared from compound 130B following the methods described above in Example 129. MS 373.2, HPLC 2.67.

Example 131

131A.

(131A)

Compound 131A was prepared in the same manner as described above for compound 129C by coupling the thiazole acid chloride with 3-aminobenzylamine. The crude product was purified via preparative HPLC and stored as the TFA salt.

131B. Example 131

To a solution of compound 131A (0.06 mmol) in CH$_2$Cl$_2$ (1 mL) at 0° C. was added DIPEA (0.24 mmol), followed by acetyl chloride (0.07 mmol). The reaction was stirred for 2 h at room temperature and the solvents removed. Water (0.5 mL) and EtOH (0.5 mL) were added, and the resulting solids filtered and purified via preparative HPLC to give Example 131 (13.1 mg, TFA salt) LCMS 347.2 (M+H); HPLC rt 2.62 min (Condition A).

Example 132

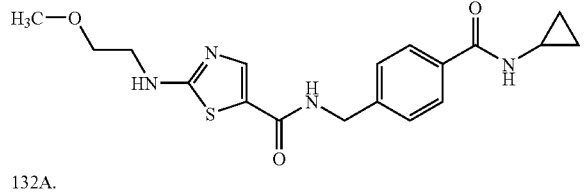

132A.

(132A)

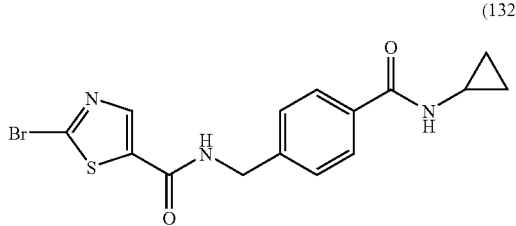

Compound 132A was prepared by coupling compound 130B with compound 1C according to the method outlined in Example 1, Step E.

132B. Example 132

Example 132 was prepared by reacting compound 132A with 2-methoxyethylamine according to the procedure outlined for Example 1. LCMS, 375.2 (M+H); HPLC rt 2.48 min (Condition A).

Example 133

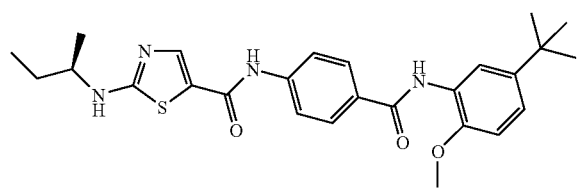

133A.

(133A)

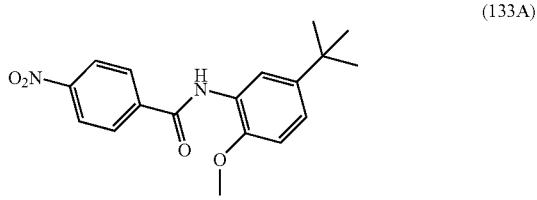

A solution of 2-methoxy-5-tert-butyl aniline (265 mg, 1.48 mmol) in CH₂Cl₂ was cooled to 0° C., and p-nitrobenzoyl chloride (274 mg, 1.48 mmol) and DIPEA (258 µL, 1.48 mmol) were added. The reaction was stirred for 10 min and the solvents removed. Water (6 mL) was added and the solids stirred rapidly for 1 h, filtered, and washed with water to give pure compound 133A (471 mg, 97% yield). LCMS 329.1 (M+H); HPLC rt 4.29 min, 99% purity.

133B.

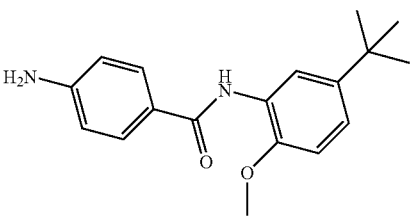

(133B)

Compound 133A was reduced to the aniline 133B using the procedure outlined for compound 1D using 1 atm hydrogen.

133C.

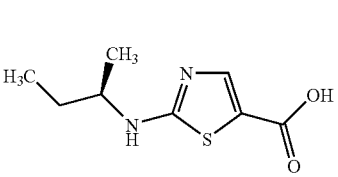

(133C)

Compound 133C was prepared according to the method outlined for compound 38F, using the appropriate thiourea.

133D. Example 133

To compound 133C (21.2 mg, 0.11 mmol) and Compound 133B (31.6 mg, 0.11 mmol) in NMP (1 mL) was added HATU (40 mg, 0.11 mmol), and the reaction mixture was heated at 70° C. for 24 h. The reaction was cooled to rt and water (2 mL) added. The organic layer was extracted with EtOAc/hexane (1/1 mixture, 2-fold), dried over Na₂SO₄, filtered, and concentrated to an oil which was purified via column chromatography (50% EtOAc/hexane) to furnish Example 133 (913 mg, 26% yield): LCMS 481.3 (M+H); HPLC rt 4.26 min, 96.5% purity.

Examples 134–143

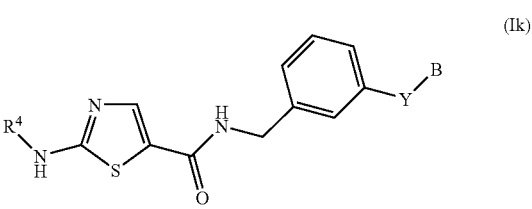

(Ik)

Compounds having the above formula (Ik), wherein $R^4$, Y and B have the values reported in Table 9, below, were prepared following the same or similar methods as described above for Examples 1, 38, 67, and 129–133.

TABLE 9

| Ex. No. | R⁴ | Y | Data MS/HPLC |
|---|---|---|---|
| 134 | —CH(CH₃)—CH₂—CH₃ | —C(=O)—N(CH₃)₂ | 361.2, 2.65 |
| 135 | —CH(CH₃)—CH₂—CH₃ | —C(=O)—NH₂ | 333.1, 2.26 |
| 136 | —CH(CH₃)—CH₂—CH₃ | —C(=O)—NH—CH₃ | 347.2, 2.42 |
| 137 | —CH(CH₃)—CH₂—CH₃ | —C(=O)—NH—CH(CH₃)₂ | 375.3, 2.87 |
| 138 | —CH(CH₃)—CH₂—CH₃ | —C(=O)—NH—CH₂CH₂CH₃ | 375.2, 2.93 |
| 139 | —CH(CH₃)—CH₂—CH₃ | —C(=O)—NH—cyclopropyl | 373.3, 2.76 |
| 140 | —CH(CH₃)—CH₂—CH₃ | —C(=O)—NH—CH₂CH₃ | 361.2, 2.63 |
| 141 | —CH(CH₃)—CH₂—CH₃ | —NH—C(=O)—CH₃ | 347.2, 2.62 |
| 142 | —CH(CH₃)—CH₂—CH₃ | —NH—C(=O)—CH₂CH₃ | 361.2, 2.88 |
| 143 | —CH(CH₃)—CH₂—CH₃ | —NH—C(=O)—O—CH₂CH₃ | 377.3, 3.11 |

Examples 144–159

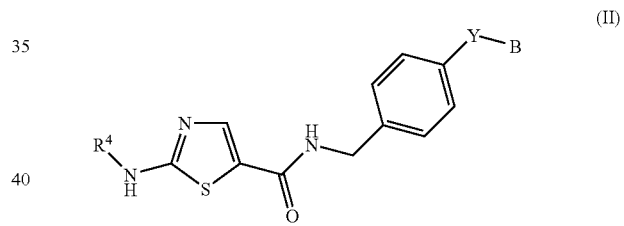

(II)

Compounds having the above formula, wherein R⁴ and Y—B together have the values reported in Table 10, below, were prepared following the same or similar methods as described above for Examples 1, 38, 67, and 129–133.

TABLE 10

| Ex. No. | R⁴ | Y—B | Data MS/HPLC |
|---|---|---|---|
| 144 | —CH(CH₃)—CH₂—CH₃ | —C(=O)—NH—CH₃ | 347.1, 2.39 |
| 145 | —CH(CH₃)—CH₂—CH₃ | —C(=O)—NH—cyclopropyl | 373.2, 2.67 |

TABLE 10-continued

| Ex. No. | R⁴ | Y—B | Data MS/HPLC |
|---|---|---|---|
| 146 | -CH(CH₃)-CH₂-CH₃ | -C(=O)-N(CH₃)₂ | 361.2, 2.66 |
| 147 | -CH(CH₃)-CH₂-CH₃ | -C(=O)-NH-CH₂-CH₃ | 361.2, 2.60 |
| 148 | -CH(CH₃)-CH₂-CH₃ | -C(=O)-NH₂ | 333.2, 2.28 |
| 149 | -CH(CH₃)-CH₂-CH₃ | -NH-C(=O)-CH₂-CH₃ | 361.1, 2.69 |
| 150 | -CH(CH₃)-CH₂-CH₃ | -NH-C(=O)-CH₃ | 347.2, 2.48 |
| 151 | -CH(CH₃)-CH₂-CH₃ | -NH-C(=O)-O-CH₂-CH₃ | 377.1, 3.50 |
| 152 | -CH₂-CH₂-CH₃ | -C(=O)-NH-cyclopropyl | 359.3, 2.49 |
| 153 | -CH₂-CH(CH₃)-CH₃ | -C(=O)-NH-cyclopropyl | 373.2, 3.20 |
| 154 | -CH₂-CH₂-OCH₃ | -C(=O)-NH-cyclopropyl | 375.2, 2.48 |
| 155 | -CH₂-CH₂-OH | -C(=O)-NH-cyclopropyl | 361.2, 2.29 |
| 156 | -CH-(CH₃)₂ | -C(=O)-NH-cyclopropyl | 359.2, 2.85 |

TABLE 10-continued

| Ex. No. | R⁴ | Y—B | Data MS/HPLC |
|---|---|---|---|
| 157 | —CH(CH₃)—CH₂—CH₃ | —C(=O)NH-cyclopropyl | 373.2, 2.80 |
| 158 | —CH(CH₃)—CH₂—CH₃ | —C(=O)NH-(2-methoxy-5-tert-butylphenyl) | 495.3, 3.87 |
| 159 | —CH(CH₃)—CH₂—CH₃ | —C(=O)NH-(2-methoxy-5-methylphenyl) | 453.2, 3.54 |

Examples 160–164

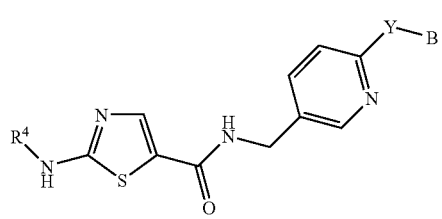
(Im)

Compounds having the above formula, wherein R⁴ and Y—B together have the values reported in Table 11, below, were prepared following the same or similar methods as described above for Examples 1, 38, 67, and 129–133.

TABLE 11

| Ex. No. | R⁴ | Y—B | Data MS/HPLC |
|---|---|---|---|
| 160 | —CH(CH₃)—CH₂—CH₃ | —C(=O)NH—CH₂CH₃ | 362.2, 2.60 |
| 161 | —CH(CH₃)—CH₂—CH₃ | —C(=O)NH-cyclopropyl | 374.2, 2.85 |
| 162 | —CH(CH₃)—CH₂—CH₃ | —C(=O)NH—CH₃ | 348.1, 2.44 |

TABLE 11-continued

| Ex. No. | R⁴ | Y—B | Data MS/HPLC |
|---|---|---|---|
| 163 | —CH(CH₃)—CH₂—CH₃ | —C(=O)NH₂ | 334.1, 2.20 |
| 164 | —CH(CH₃)—CH₂—CH₃ | —NH—C(=O)O—CH₂CH₃ | 378.2, 2.43 |

What is claimed is:

1. A compound having the formula (I),

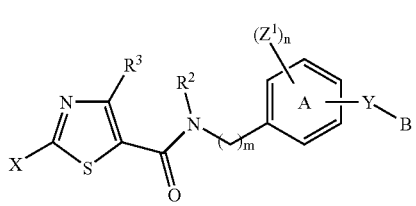

enantiomers, diastereomers, pharmaceutically-acceptable salts, and solvates thereof, wherein, ring A is phenyl;
Y is —C(=O)NR¹— and is attached to the phenyl ring in the meta or para position;
R¹ is
  (a) hydrogen;
B is
  (a) hydrogen;

R² is
 (a) hydrogen;
R³ is hydrogen;
X is
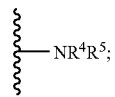
R⁴ and R⁵ are independently
 (a) hydrogen; or
Z¹ is an optional substituents independently selected from
 (1) R¹⁰, where R¹⁰ is
  (i) alkyl; or
  (ii) a group (i) which is itself substituted by one to four of the same or different groups (i);
m is 0; and
n is 1.
2. A compound according to claim 1 having the formula,
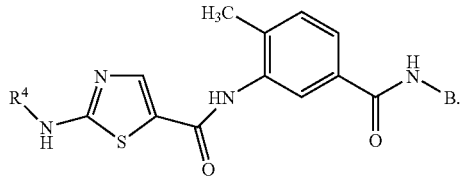
* * * * *

UNITED STATES PATENT AND TRADEMARK OFFICE
CERTIFICATE OF CORRECTION

PATENT NO.       : 7,169,771 B2
APPLICATION NO.  : 10/773790
DATED            : January 30, 2007
INVENTOR(S)      : John Hynes et al.

It is certified that error appears in the above-identified patent and that said Letters Patent is hereby corrected as shown below:

Claim 1, column 67, line 12, delete "substitutents" and insert -- substituent --.

Signed and Sealed this

Fifteenth Day of May, 2007

JON W. DUDAS
*Director of the United States Patent and Trademark Office*